US012788590B2

(12) United States Patent
Semler et al.

(10) Patent No.: US 12,788,590 B2
(45) Date of Patent: Nov. 10, 2026

(54) ARTICULATING EXPANDABLE DEVICE

(71) Applicant: MUSC Foundation for Research Development, Charleston, SC (US)

(72) Inventors: Mark Semler, Mt. Pleasant, SC (US); Joe Ruscito, Charleston, SC (US); Stephen Kalhorn, Mt. Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 86 days.

(21) Appl. No.: 18/571,018

(22) PCT Filed: Jun. 22, 2022

(86) PCT No.: PCT/US2022/034514
§ 371 (c)(1),
(2) Date: Dec. 15, 2023

(87) PCT Pub. No.: WO2022/271816
PCT Pub. Date: Dec. 29, 2022

(65) Prior Publication Data

US 2024/0277488 A1 Aug. 22, 2024

Related U.S. Application Data

(60) Provisional application No. 63/213,282, filed on Jun. 22, 2021.

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/4425* (2013.01); *A61F 2002/30471* (2013.01);
(Continued)

(58) Field of Classification Search
CPC ............................ A61F 2/4611; A61F 2/4425
See application file for complete search history.

(56) References Cited

U.S. PATENT DOCUMENTS 10,111,755 B2 10/2018 Foley
10,485,675 B2 11/2019 Sharifi-Mehr
(Continued)

FOREIGN PATENT DOCUMENTS

DE 102018206693 2/2019
WO WO-2019068074 A1 * 4/2019 .......... A61F 2/4455

OTHER PUBLICATIONS

Extended European Search Report issued in App. No. EP22829223, dated Jun. 10, 2025, 14 pages.
(Continued)

*Primary Examiner* — Matthew J Lawson
(74) *Attorney, Agent, or Firm* — Riverside Law LLP

(57) ABSTRACT

The present invention provides articulating expandable devices and insertion tools for deploying the articulating expandable devices. The articulating expandable devices are capable of being inserted into narrow spaces and turning around corners. The articulating expandable devices are capable of increasing in height and width when expanded from a closed configuration to an open configuration to occupy a larger volume and to present a larger surface area. The articulating expandable devices are lockable and are capable of rigidly occupying a space after expansion. In some embodiments, the articulating expandable devices are useful as interbody devices for spinal fusions.

15 Claims, 21 Drawing Sheets

(52) U.S. Cl.
CPC ............... *A61F 2002/30476* (2013.01); *A61F 2002/4622* (2013.01); *A61F 2002/4628* (2013.01); *A61F 2002/4681* (2013.01)

(56) References Cited

U.S. PATENT DOCUMENTS

| | | | | |
|---|---|---|---|---|
| 11,000,385 | B2 | 5/2021 | Kalhorn | |
| 11,109,980 | B2 | 9/2021 | Seifert | |
| 2007/0255415 | A1* | 11/2007 | Edie | A61F 2/4611 606/90 |
| 2009/0234364 | A1* | 9/2009 | Crook | A61F 2/4465 606/99 |
| 2011/0301712 | A1* | 12/2011 | Palmatier | A61F 2/4611 623/17.16 |
| 2012/0197299 | A1* | 8/2012 | Fabian, Jr. | A61F 2/442 606/279 |
| 2014/0052253 | A1 | 2/2014 | Perloff | |
| 2015/0327765 | A1 | 11/2015 | Crane | |
| 2017/0056200 | A1* | 3/2017 | Koch | A61F 2/4611 |
| 2022/0015923 | A1* | 1/2022 | Shoshtaev | A61F 2/4455 |
| 2022/0214851 | A1* | 7/2022 | Matsushita | H04N 7/0127 |

OTHER PUBLICATIONS

Partial Supplementary European Search Report issued in App. No. EP22829223, dated Mar. 19, 2025, 15 pages.

* cited by examiner

ARTICULATING EXPANDABLE DEVICE

CROSS-REFERENCE TO RELATED APPLICATIONS

This application is a U.S. national stage filing of international application No. PCT/US22/34514, filed Jun. 22, 2022, which claims priority to U.S. provisional application No. 63/213,282 filed on Jun. 22, 2021, both of which are incorporated herein by reference in its their entireties.

BACKGROUND OF THE INVENTION

Certain spinal fusion procedures remove degenerated intervertebral disc material and pack the intervertebral space to maintain the separation between adjacent vertebrae. While some procedures pack the intervertebral space with bone-forming tissue, other procedures insert rigid devices for more reliable separation of the vertebrae. In the interest of reducing recovery time and surgical tissue damage, it is advantageous for a rigid device insert to possess a small profile to fit through a minimally invasive incision and to steer around corners, while also possessing a large footprint to maximize stability in the intervertebral disc space.

Thus, there is a need in the art for small profile rigid devices that are able to navigate corners and expand to occupy a larger footprint. The present invention satisfies this need.

SUMMARY OF THE INVENTION

In one aspect, the present invention relates to an articulating expandable device, comprising: a first and a second superior arm and a first and a second inferior arm; the first superior arm further comprising a hinged connector extending from its posterior end; and the second superior arm further comprising a socket extending from its posterior end.

In one embodiment, each arm possesses an anterior and a posterior end and a top and a bottom surface, and each arm having an anterior and posterior opening through the top and bottom surface, wherein the first superior arm is positioned over the first inferior arm with anterior and posterior openings in alignment, and the second superior arm is positioned over the second inferior arm with anterior and posterior openings in alignment.

In one embodiment, the device further comprises: four cylindrical bolts positioned within each of the openings of the arms; a first rod connecting each of the bolts positioned within the anterior openings of the arms; and a second rod connecting each of the bolts positioned within the posterior openings of the arms.

In one embodiment, the cylindrical bolts further comprise: a top end, a bottom end, an outer surface, and at least one upper curved slot and at least one lower curved slot extending through each bolt, wherein each curved slot has a closed position near a center of each bolt, each of the at least one upper curved slot has an open position near the top end of each bolt, and each of the at least one lower curved slot has an open position near the bottom end of each bolt.

In one embodiment, the device further comprises a plurality of pins, each pin connected to an inner surface of each of the openings of the arms and slidably engaged to a curved slot of the bolt positioned within the respective opening.

In one embodiment, each of the four arms are substantially parallel to each other in a closed configuration. In one embodiment, the four arms are movable about the four bolts while maintaining substantially parallel alignment to each other.

In one embodiment, the device comprises a closed configuration that positions the four arms adjacent to each other and positions the plurality of pins near the center of each bolt. In one embodiment, the device comprises an open configuration that positions the four arms away from each other and positions the plurality of pins near the top and bottom ends of each bolt. In one embodiment, at least one arm comprises a locking bit drivable into a bolt.

In one aspect, the present invention relates to an insertion tool, comprising: a posterior handle having a rotating section, a nonrotating section, and a lumen running throughout; an expandable pair of tongs extending from the nonrotating section in an anterior direction, the tongs having a hinged anterior connector; a locking sleeve slidable over the pair of tongs; and an elongate deployment driver positioned within the lumen of the housing, the deployment driver having a hingedly connected driver horn.

In one embodiment, anterior and posterior movement of the locking sleeve is lockable using a backstop. In one embodiment, actuating the rotating section of the housing moves the deployment driver in an anterior or posterior direction. In one embodiment, the locking sleeve comprises a wedge positioned between each member of the pair of tongs, such that posterior sliding of the locking sleeve expands the pair of tongs.

In one aspect, the present invention relates to an articulating expandable device kit, comprising: an articulating expandable device comprising: a first and a second superior arm and a first and a second inferior arm, each arm having an anterior and a posterior end and a top and a bottom surface, and each arm having an anterior and posterior opening through the top and bottom surface, wherein the first superior arm is positioned over the first inferior arm with anterior and posterior openings in alignment, and the second superior arm is positioned over the second inferior arm with anterior and posterior openings in alignment; four cylindrical bolts positioned within each of the openings of the arms, each bolt having a top end, a bottom end, an outer surface, and at least one upper curved slot and at least one lower curved slot extending through each bolt, wherein each curved slot has a closed position near a center of each bolt, each of the at least one upper curved slot has an open position near the top end of each bolt, and each of the at least one lower curved slot has an open position near the bottom end of each bolt; a first rod connecting each of the bolts positioned within the anterior openings of the arms, and a second rod connecting each of the bolts positioned within the posterior openings of the arms; and a plurality of pins, each pin connected to an inner surface of each of the openings of the arms and slidably engaged to a curved slot of the bolt positioned within the respective opening; wherein the first superior arm comprises a hinged connector extending from its posterior end, and the second superior arm comprises a socket extending from its posterior end; and an insertion tool comprising: a posterior handle having a rotating section, a nonrotating section, and a lumen running throughout; an expandable pair of tongs extending from the nonrotating section in an anterior direction, the tongs having a hinged anterior connector engageable to the hinged connector of the articulating expandable device; a locking sleeve slidable over the pair of tongs; and an elongate deployment driver positioned within the lumen of the housing, the deployment driver having a hingedly connected driver horn engageable to the socket of the articulating expandable device.

In one embodiment, the articulating expandable device is configured to removably attach to the insertion tool in a closed configuration by hingedly engaging the connector to the tongs and the socket to the driver horn. In one embodiment, actuating the rotating section of the housing moves the deployment driver in an anterior direction and articulates the articulating expandable device about the hinged engagement between the connector and the tongs.

In one embodiment, the articulating expandable device is articulated by an angle between a longitudinal axis of the articulating expandable device and a longitudinal axis of the insertion device. In one embodiment, the angle is between about 1 degrees and 180 degrees. In one embodiment, the angle is between about 181 degrees and 360 degrees.

In one embodiment, the articulation of the articulating expandable device is limited by a physical stop. In one embodiment, further actuation of the rotating section of the housing moves the deployment driver in an anterior direction and expands the articulating expandable device to an open configuration. In one embodiment, the locking sleeve comprises a lumen having a locking bit driver configured to drive a locking bit into the articulating expandable device, such that the articulating expandable device is locked in the open configuration.

In one embodiment, the open configuration of the articulating expandable device is any configuration other than a closed configuration. In one embodiment, the locking sleeve comprises a wedge positioned between each member of the pair of tongs, such that posterior sliding of the locking sleeve expands the pair of tongs and releases the articulating expandable device from the insertion device.

In one embodiment, a deployment instrument includes a proximal handle, a stabilization retainer extending parallel to a central axis from the proximal handle to a distal end of the deployment instrument, and a deployment driver extending parallel to the stabilization retainer along the central axis, the deployment driver including at its distal end a hingedly connected pivot arm, wherein at least one of the stabilization retainer and deployment driver is translatable along the central axis. In one embodiment, only the deployment driver is translatable along the central axis. In one embodiment, the deployment driver is slidably translatable along the central axis. In one embodiment, the proximal handle includes one or more features selected from the group consisting of (i) an actuator that drives translation of the deployment driver along the central axis, the actuator comprising a mechanism selected from the group consisting of sliding rail, ratchet, worm gear, screw, cam and follower, lever, gear, spring, and combinations thereof; (ii) a slap hammer surface; and (iii) combinations thereof. In one embodiment, the proximal handle includes an actuator that drives translation of the deployment driver along the central axis, the actuator comprising corresponding threaded engagement between a proximal portion of the deployment driver and a housing portion of the proximal handle, wherein the threaded engagement can drive movement of the deployment driver along the central axis. In one embodiment, the proximal handle includes a lock that prevents actuation of translation of the deployment driver along the central axis. In one embodiment, one or both of the stabilization retainer and the pivot arm of the deployment is forked at its distal end the forks including opposing pins that form a hinged connector with a pivot axis. In one embodiment, only the stabilization retainer is forked at its distal end, the fork including opposing pins that form a hinged connector with a pivot axis. In one embodiment, the stabilization retainer includes at its distal end a pair of retaining pins oriented along an axis that is transverse to the central axis and forming a hinged connector. In one embodiment, the stabilization retainer includes at its distal end a pair of opposing fork arms and a pair of opposing retaining pins, each one of the pair of retaining pins oriented distally on a fork arm, the opposing pair of retaining pins forming a hinged connector. In one embodiment, the device includes a locking sleeve that is slidable along the central axis over the stabilization retainer to releasably compress the opposing fork arms. In one embodiment, the locking sleeve comprises a wedge that is positionable between the opposing fork arms, such that when the wedge is positioned most distally relative to the fork arms, the fork arms are in a relaxed orientation, and when the wedge is moved proximally by translation of the sleeve proximally along the stabilization retainer, the wedge contacts the opposing fork arms into an expanded orientation and the opposing retaining pins are displaced away from each other. In one embodiment, the proximal handle includes a lock that retains the locking sleeve in place to compress the opposing fork arms. In one embodiment, the hingedly connected pivot arm on the deployment driver includes a pair of retaining pins oriented along an axis that is transverse to the central axis and forming a hinged connector, wherein each of the retaining pins projects outward from the pivot arm. In one embodiment, the hingedly connected pivot arm on the deployment driver includes at its distal end a pair of opposing fork arms and a pair of opposing retaining pins, each one of the pair of retaining pins oriented distally on a fork arm, the pair of opposing retaining pins forming a hinged connector.

In one embodiment, a deployment instrument, includes a proximal handle, a stabilization retainer extending parallel to a central axis from the proximal handle to a distal end of the deployment instrument, the stabilization retainer including at its distal end a first pair of retaining pins oriented along an axis that is transverse to the central axis, and a deployment driver extending parallel to the stabilization retainer along the central axis, the deployment driver including at its distal end a hingedly connected pivot arm, the pivot arm including at a distal end a second pair of retaining pins, wherein at least one of the stabilization retainer and deployment driver is slidably translatable along the central axis.

In one embodiment, a deployment instrument includes a proximal handle, a stabilization retainer extending parallel to a central axis from the proximal handle to a distal end of the deployment instrument, the stabilization retainer including at its distal end a pair of opposing fork arms and a pair of opposing retaining pins, each one of the pair of retaining pins oriented distally on a fork arm, the opposing pair of retaining pins forming a hinged connector, a locking sleeve that is slidable along the central axis over the stabilization retainer to releasably compress the opposing fork arms, the locking sleeve comprising a wedge that is positionable between the opposing fork arms, such that when the wedge is positioned most distally relative to the fork arms, the fork arms are in a relaxed orientation, and when the wedge is moved proximally by translation of the sleeve proximally along the stabilization retainer, the wedge contacts the opposing fork arms into an expanded orientation and the opposing retaining pins are displaced away from each other, and a deployment driver extending parallel to the stabilization retainer along the central axis, the deployment driver including at its distal end a hingedly connected pivot arm, the pivot arm including at its distal end a pair of retaining pins oriented along an axis that is transverse to the central axis and forming a hinged connector, wherein each of the retaining pins projects outward from the pivot arm, wherein the handle includes an actuator that drives translation of the deployment driver along the central axis, the actuator comprising a mechanism the proximal handle includes one or more features selected from the group consisting of (i) an actuator that drives translation of the deployment driver along the central axis, the actuator comprising a mechanism selected from the group consisting of sliding rail, ratchet, worm gear, screw, cam and follower, lever, gear, spring, and combinations thereof; (ii) a slap hammer surface; and (iii) combinations thereof.

In one embodiment, an articulating expandable device kit includes an articulating expandable device having a first and a second superior arm and a first and a second inferior arm, the first superior arm further comprising a hinged connector extending from its posterior end, and the second superior arm further comprising a socket extending from its posterior end; and a deployment instrument having a proximal handle, a stabilization retainer extending parallel to a central axis from the proximal handle to a distal end of the deployment instrument, and a deployment driver extending parallel to the stabilization retainer along the central axis, the deployment driver including at its distal end a hingedly connected pivot arm, wherein at least one of the stabilization retainer and deployment driver is translatable along the central axis. In one embodiment, the articulating expandable device is configured to removably attach to the deployment instrument in a closed configuration by hingedly engaging the connector to the stabilization retainer and engaging the socket to the pivot arm of the deployment driver wherein the articulating expandable device includes positive stop features that retain the articulating expandable device in the closed configuration that is aligned with the central axis of the deployment instrument, and wherein actuating translation of the deployment driver along the central axis to drive the pivot arm distally, the pivot arm is driven to rotate driving the engaged socket to translate the articulating expandable device into an open configuration and oriented substantially transverse to the central axis.

In one embodiment, a method for deployment of an articulating an expandable device into a space between adjacent vertebral bodies includes the steps of providing the expandable device comprising a first and a second superior arm and a first and a second inferior arm, the first superior arm further comprising a hinged connector extending from its posterior end, and the second superior arm further comprising a socket extending from its posterior end; removably affixing the articulating expandable device to the deployment instrument in a closed configuration by hingedly engaging the connector to the stabilization retainer and engaging the socket to the pivot arm of the deployment driver; retaining the articulating expandable device in the closed configuration that is aligned with the central axis of the deployment instrument while passing the device as retained on the deployment instrument into a space between two adjacent vertebral bodies at a first orientation that is oblique to an anterior to posterior axis of the adjacent vertebral bodies; actuating the deployment driver of the deployment instrument along the instrument's central axis to rotate the articulating expandable device into an open configuration and oriented substantially transverse to the central axis to direct the device in a second orientation that is generally oriented transverse to the anterior to posterior axis of the adjacent vertebral bodies; passing an expansion driver adjacent the deployment instrument and into engagement articulating expandable device to expand the articulating expandable device in a cephaloncaudal dimension and into compressive contact with the vertebral bodies; and actuating the locking bit of the articulating expandable device to fix the device into a locked configuration. In one embodiment, the method includes initially driving the articulating expandable device into the surgical site by hammering on a slap hammer surface at the proximal handle of the deployment instrument. In one embodiment, the method includes actuating release of the stabilization retainer from the articulating expandable device. In one embodiment, the method includes expanding the articulating expandable device results in the release of the pivot arm of the deployment driver.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

DETAILED DESCRIPTION

Figure 1C:
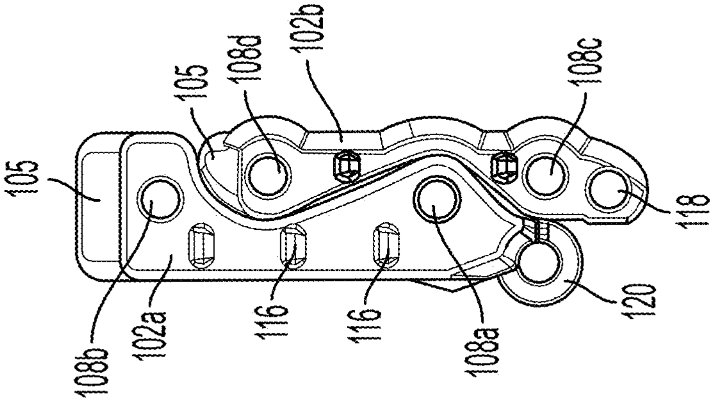
FIGS. 1A, 1B and 1C depict a posterior perspective view (top, 1A), an anterior perspective view (bottom, 1B), and a top view (right, 1C) of an exemplary articulating expandable device in a closed configuration according to one embodiment.

The present invention provides articulating expandable devices and insertion tools for deploying the articulating expandable devices. The articulating expandable devices are capable of being inserted into narrow spaces and turning around corners. The articulating expandable devices are capable of increasing in height and width when expanded from a closed configuration to an open configuration to occupy a larger volume and to present a larger surface area. The articulating expandable devices are lockable and are capable of rigidly occupying a space after expansion. In some embodiments, the articulating expandable devices are useful as interbody devices for spinal fusions.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Articulating Expandable Device

Figure 1A:
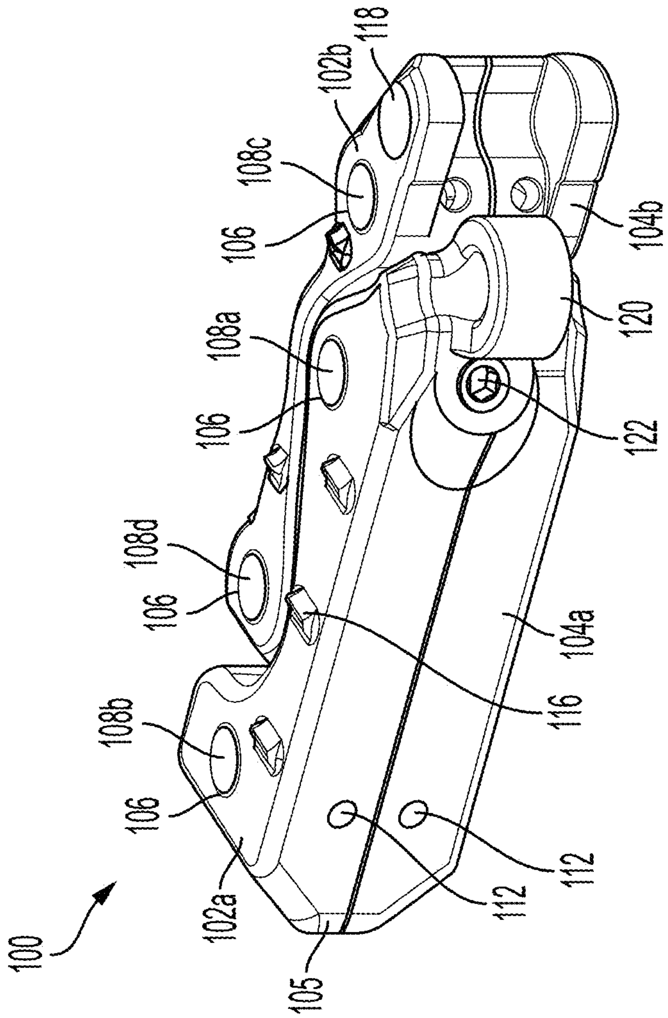
Figure 1B:
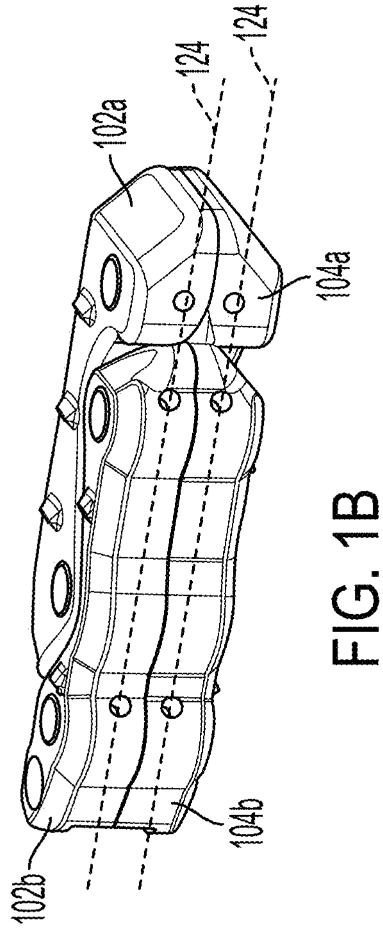

Referring now to FIGS. 1A-1C, an exemplary articulating expandable device 100 is depicted. Device 100 comprises four arms (superior first arm 102*a*, superior second arm 102*b*, inferior third arm 104*a*, and inferior fourth arm 104*b*) and four movable bolts 108 (referred to herein as posterior first bolt 108*a*, anterior second bolt 108*b*, posterior third bolt 108*c*, and anterior fourth bolt 108*d*). Each arm comprises two slots 106 sized to fit a movable bolt 108. Each bolt 108 is secured within a slot 106 by a pin 112 fixed to each arm, and bolts 108*a*-108*d* are secured in pairs by a connecting rod 110 (108*a* connected to 108*c* by connecting rod 110*a*, 108*b* connected to 108*d* by connecting rod 110*b*, shown in FIG. 2).

Arms 102*a*, 102*b*, 104*a*, 104*b*, bolts 108*a*-108*d*, and pins 112 are preferably constructed from a rigid material, such as a metal or a hard polymer such as PEEK. In various embodiments, the rigid material is a biocompatible material. In certain embodiments, each arm can comprise a surface that is textured or at least partially covered with barbs or spikes 116 to improve the attachment of device 100 within a space. In certain embodiments, each arm can terminate in a taper 105 at an anterior end, wherein taper 105 facilitates entry of expandable device 100 into a space.

In various embodiments, each arm can comprise a plurality of cavities. The cavities may be placed throughout each arm without compromising the rigidity of device 100. The cavities can be filled with any component that is synergistic with the function of device 100. For example, in some embodiments, the cavities can be packed with a biological material to promote the ingrowth of tissue, such as bone. In some embodiments, the cavities can be packed with a therapeutic to treat surrounding tissue. In some embodiments, one or more sensors can be inserted into the cavities to monitor the device and its environs, such as a temperature sensor, pressure sensor, corrosion sensor, and the like. In some embodiments, the cavities can be used to secure device 100 within a space, such as by accepting screws or cement. The cavities can also be used to view and monitor the progress of bone growth into the interior of device 100.

In some embodiments, an arm may further comprise features for engaging an insertion tool, described elsewhere herein. For example, arm 102*a* can comprise connector 120 sized to mate with an insertion tool. Connector 120 may be a hinged connector as shown in FIGS. 1A-1C to rotatably engage an insertion tool. Arm 102*a* can further comprise a locking bit 122 that can be driven to lock into a bolt 108 (such as bolt 108*a*), thereby arresting movement in device 100. In another example, arm 102*b* can comprise socket 118 to fit the driver horn of an insertion tool, described elsewhere herein.

Figure 2:
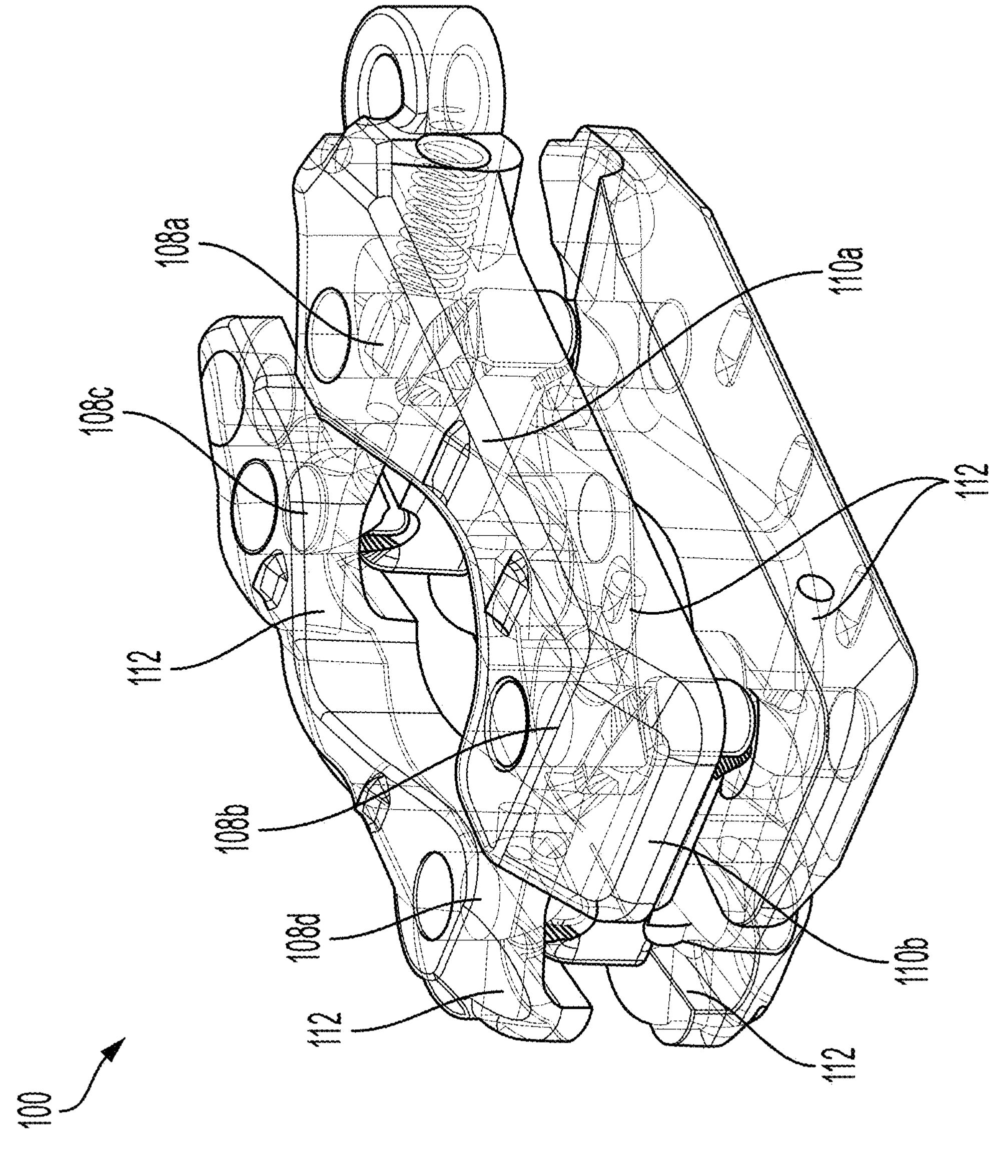
FIG. 2 depicts a partially wireframe anterior perspective view of an exemplary articulating expandable device in an open configuration according to one embodiment, such that internal bolts and crossbars are visible.
Figure 3B:
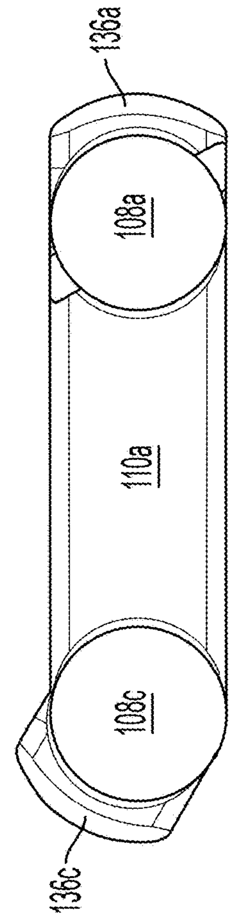
FIG. 3A and FIG. 3B depict a perspective view and a top view, respectively, of a connecting rod connecting two bolts of an exemplary expandable device according to one embodiment.
Figure 3A:
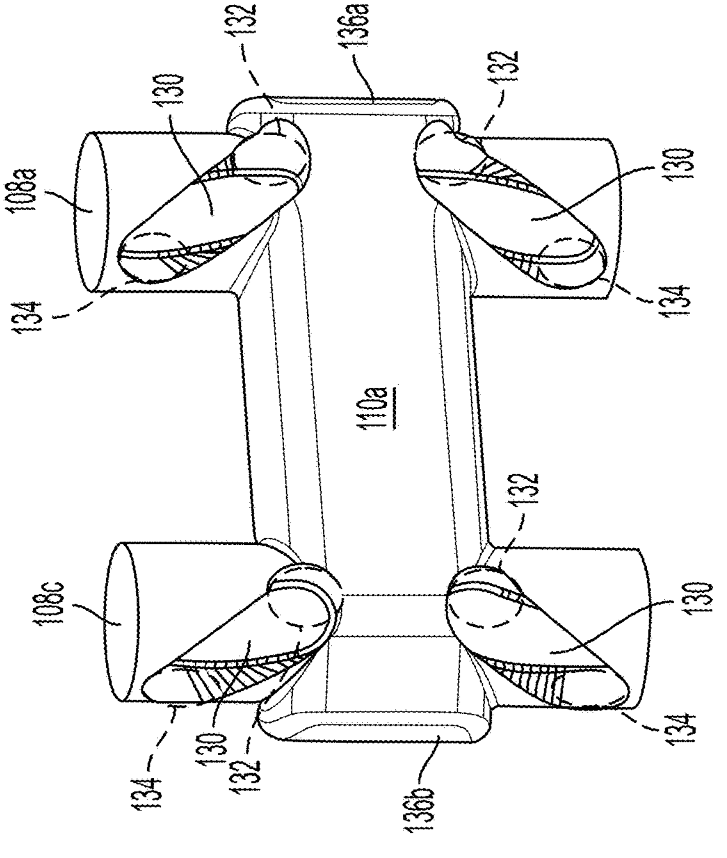

Referring now to FIG. 2 through FIG. 3B, bolts 108*a* through 108*d* are depicted with their respective crossbars 110*a* and 110*b*. Bolts 108*a*-108*d* and crossbars 110*a* and 110*b* can have any suitable dimensions. In some embodiments, bolts 108*a*-108*d* each have the same dimensions. In some embodiments, bolts 108*a*-108*d* each have different dimensions or combinations of different dimensions. Each bolt 108 comprises a cylindrical shape having a top end, a bottom end, and an outer surface. Each bolt 108 comprises four pin guides 130 cut into the outer surface (visible in FIG. 3A). Each pin guide 130 is a curved slot having a closed position 132 near the center of a bolt 108 and an open position 134 near the top and bottom ends of a bolt 108. Closed position 132 and open position 134 are placed at an angle between about 60 and 130 degrees away from each other on the outer surface. Pin guides 130 are arranged on each bolt 108 on the top half and the bottom half of each bolt 108, such that a pin 112 can extend into each pin guide 130. Rotating each bolt 108 thereby slides a pin 112 through each pin guide 130 between a closed position 134 and an open position 134. Each bolt 108 further comprises a rounded cam 136 positioned on its outer surface, midway between the top end and bottom end of each bolt 108. For example, bolt 108*a* comprises cam 136*a*, bolt 108*b* comprises cam 136*b*, bolt 108*c* comprises cam 136*c*, and bolt 108*d* comprises cam 136*d*.

Figure 4:
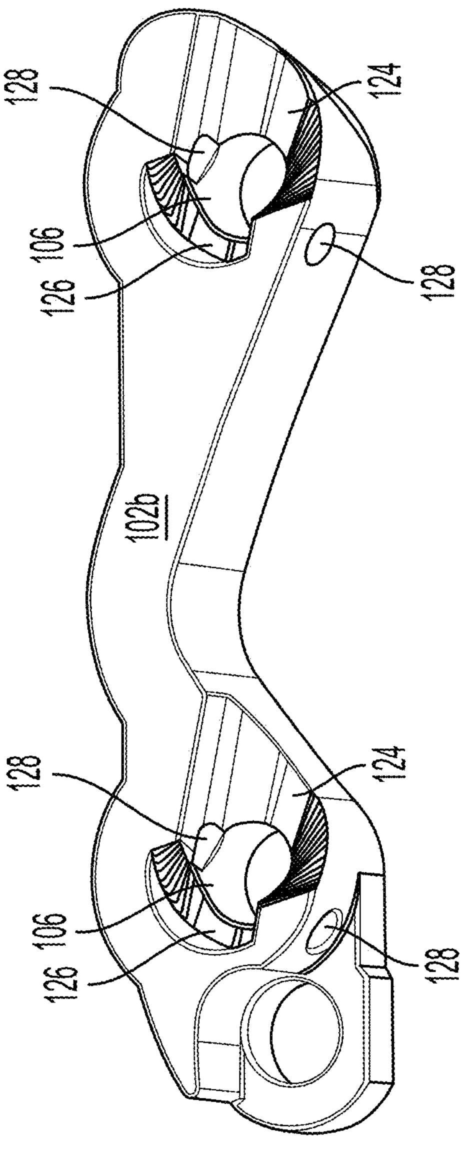
FIG. 4 depicts the interior of an arm of an exemplary expandable device in isolation according to one embodiment.

Referring now to FIG. 4, the interior of arm 102*b* is depicted. The perimeter of each slot 106 comprises a variably sloping surface upon which cams 136 of each bolt 108 and each crossbar 110 slides against as each bolt 108 rotates. For example, the variably sloping surface comprises opposing first cam faces 124 and opposing second cam faces 126. The opposing first cam faces 124 provide a sloping surface to slide a cam 136 between open and closed configurations, and the opposing second cam faces 126 provide a sloping surface to slide a crossbar 510 between open and closed configurations. Pin holes 128 are visible in each slot 106, which hold pins 112 stationary while bolts 108 are rotated. While arm 102*b* is depicted here, it should be understood that the description of the features of arm 102*b* are equally applicable to any of the arms of expandable device 100, including arm 102*a*, 104*a*, and 104*b*.

As shown in FIGS. 1A-5C and FIGS. 5A-5C, expandable device 100 has a closed configuration and an open configuration, respectively. As described above, rotating each of bolt 108*a*-108*d* shifts expandable device 100 between the closed configuration and the open configuration. The shift is achieved by two mechanisms: the first is the positioning of each pin 112 in each pin guide 130 between a closed position 132 and an open position 134; the second is the positioning of the cams 136 and crossbars 110 between the opposing first cam faces 124 and the opposing second cam faces 126 of each arm 102*a*, 102*b*, 104*a*, and 104*b*. Compressive forces acting on expandable device 100 in an open configuration are thereby supported by each pin 112 in a pin guide 130, as well as each cam face 124 and crossbar 110 pressing against the variably sloping surface on the periphery of each slot 106 at each cam face 124, each cam face 126, and positions therebetween.

The arrangement of bolts 108*a*-108*d*, pins 112, pin guides 130, cams 136, and opposing cam faces 124 and 126 synchronize the simultaneous movement between each arm 102*a*, 102*b*, 104*a*, and 104*b*. Shifting expandable device 100 from a closed configuration to an open configuration separates superior arms 102*a* and 102*b* from inferior arms 104*a* and 104*b* at the same rate and distance. Shifting expandable device 100 from a closed configuration to an open configuration also laterally separates arms 102*a* and 104*a* from arms 102*b* and 104*b*.

Figure 5C:
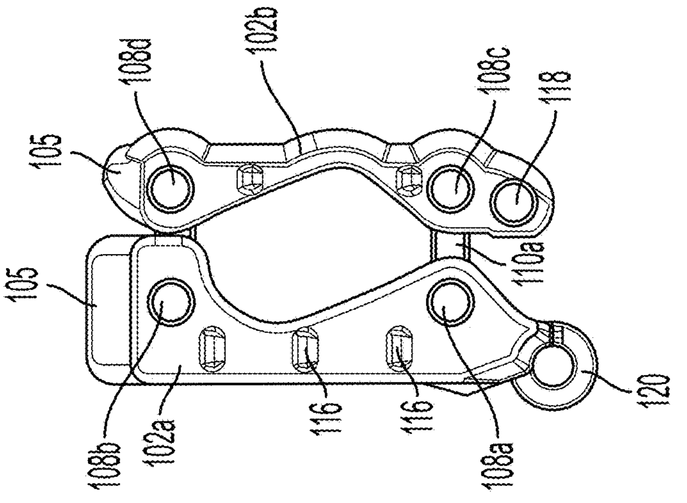
FIGS. 5A, 5B and 5C depict a posterior perspective view (top, 5A), an anterior perspective view (bottom, 5B), and a top view (right, 5C) of an exemplary articulating expandable device in an open configuration according to one embodiment.
Figure 5A:
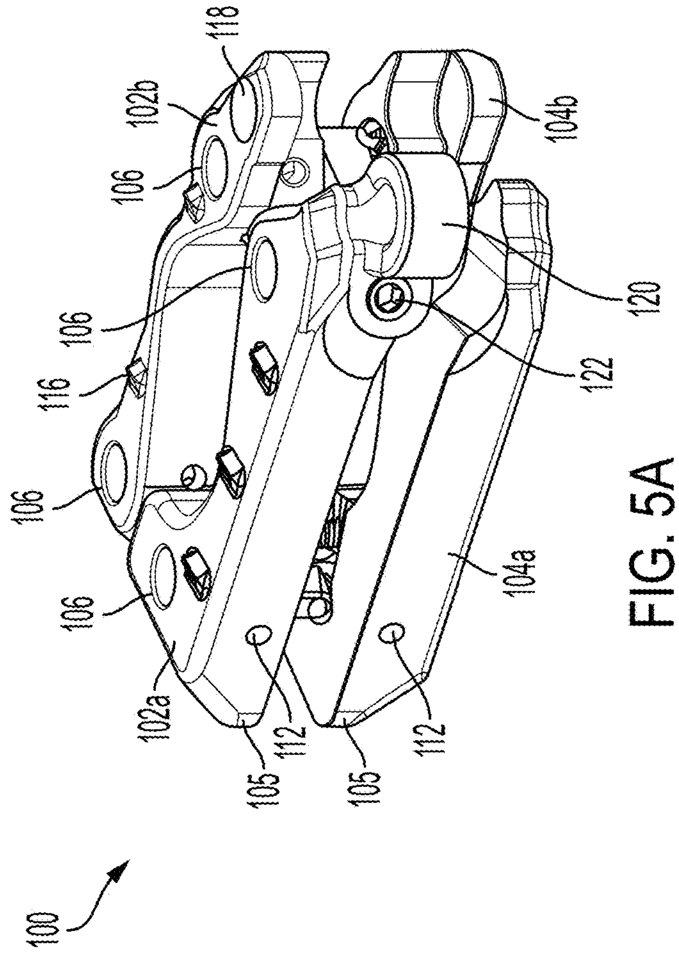
Figure 5B:
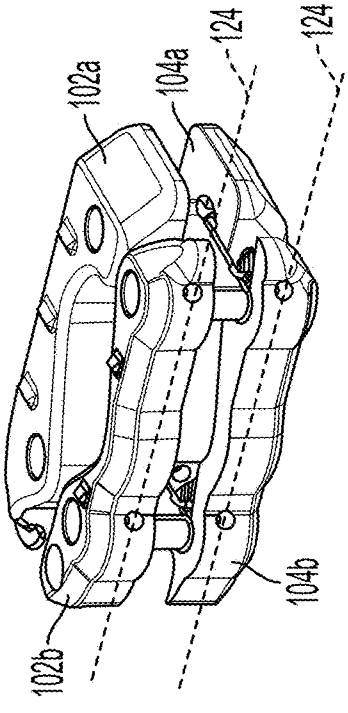

In some embodiments, arm 102*a* and 104*a* are in parallel alignment, and arm 102*b* and 104*b* are in parallel alignment, as visualized by longitudinal axis 124 running through the lengths of each arm in FIG. 1. In some embodiments, arms 102*a* and 104*a* are in parallel alignment with arms 102*b* and 104*b*. In some embodiments, arms 102*a* and 104*a* are not in parallel alignment with arms 102b and 104*b*. FIG. 5A-5C illustrates that shifting device 100 between a closed configuration and an open configuration also maintains the parallel alignment between arm 102*a* (and arm 104*a* underneath) on one side and arm 102*b* (and arm 104*b* underneath) on the opposite side (visualized by the parallel arm axes 124). FIG. 5A-5C also illustrates that shifting device 100 between a closed configuration and an open configuration induces a separation in distance between arms 102*a* and 104*a* on one side and arms 102*b* and 104*b* on the opposite side, wherein the separation is defined in part by the length of the connecting rods 110.

The exemplary device 100 is depicted as having a polyhedron-like shape with four rectangular sides and a parallelogram-like top and bottom when closed (FIG. 1), and a polyhedron-like shape with four rectangular sides and a rectangular top and bottom when open (FIG. 5A-5C). However, it should be understood that device 100 is not limited to the depicted shapes or dimensions, and can have any suitable shape or dimension. For example, each of the arms 102 and 104 can comprise a semicircular shape to give device 100 an overall cylindrical shape having curved sides and a circular or oval top and bottom. For example, the length of each of the arms 102 and/or 104 can be substantially similar to the length of the connecting rods 110 and/or bolts 108 to give any side of the device 100 an overall square shape or the entire device 100 an overall cubical shape.

In some embodiments, one or more of the connecting rods 110 can have a different length (not pictured). For example, bolt 108*a* and bolt 108*c* can be joined by a connecting rod 110*a* having a first length, and bolt 108*b* and bolt 108*d* can be joined by a connecting rod 110*b* having a second length, such that arms 102*a* and 104*a* are separated from the opposing arms 102*b* and 104*b* by the first length at one end and by a second length at an opposing end. In this manner, device 100 can thereby maintain a substantially rectangular top and bottom when closed, and has a substantially trapezoidal top and bottom when open.

In some embodiments, one or more of the bolts 108 can have pin guides with different open positions. For example, bolt 108*a* and bolt 108*c* can each have pin guides with an open position at a first height, and bolt 108*b* and bolt 108*d* can each have pin guides with an open position at a second height, such that superior arms 102*a* and 102*b* are separated from inferior arms 104*a* and 104*b* by a first height at one end and by a second height at an opposing end. In this manner, device 100 can thereby maintain substantially rectangular sides when closed, and has a lordotic angle with a substantially trapezoidal left and right side when open.

Device 100 can have any suitable dimensions between its closed and open configurations. For example, in certain embodiments, device 100 can have a closed length of between 30 mm to 30 cm, a closed width of between 7 mm to 7 cm, and a closed height of between 8 mm and 8 cm. In certain embodiments, device 100 can have an open length of between 20 mm to 20 cm, an open width of between 10 mm to 10 cm, and an open height of between 10 mm and 10 cm. The surface area and footprint of device 100 will depend on the length, width, and height, and will change accordingly between open and closed configurations. The surface area of device 100 will further depend on modifications to device 100, such as the number of cavities. In one embodiment, an exemplary device 100 has a closed length, width, and height of 34.81 mm, 7.94 mm, and 8 mm, respectively; an open length, width and height of 27.36 mm, 17.27 mm, and 10.63 mm, respectively; a closed footprint and footprint surface area of 221.16 $mm^2$ and 165.84 $mm^2$, respectively; and an open footprint and footprint surface area of 361.68 $mm^2$ and 184.02 $mm^2$, respectively.

First Insertion Tool for the First Expandable Device

Figure 6:
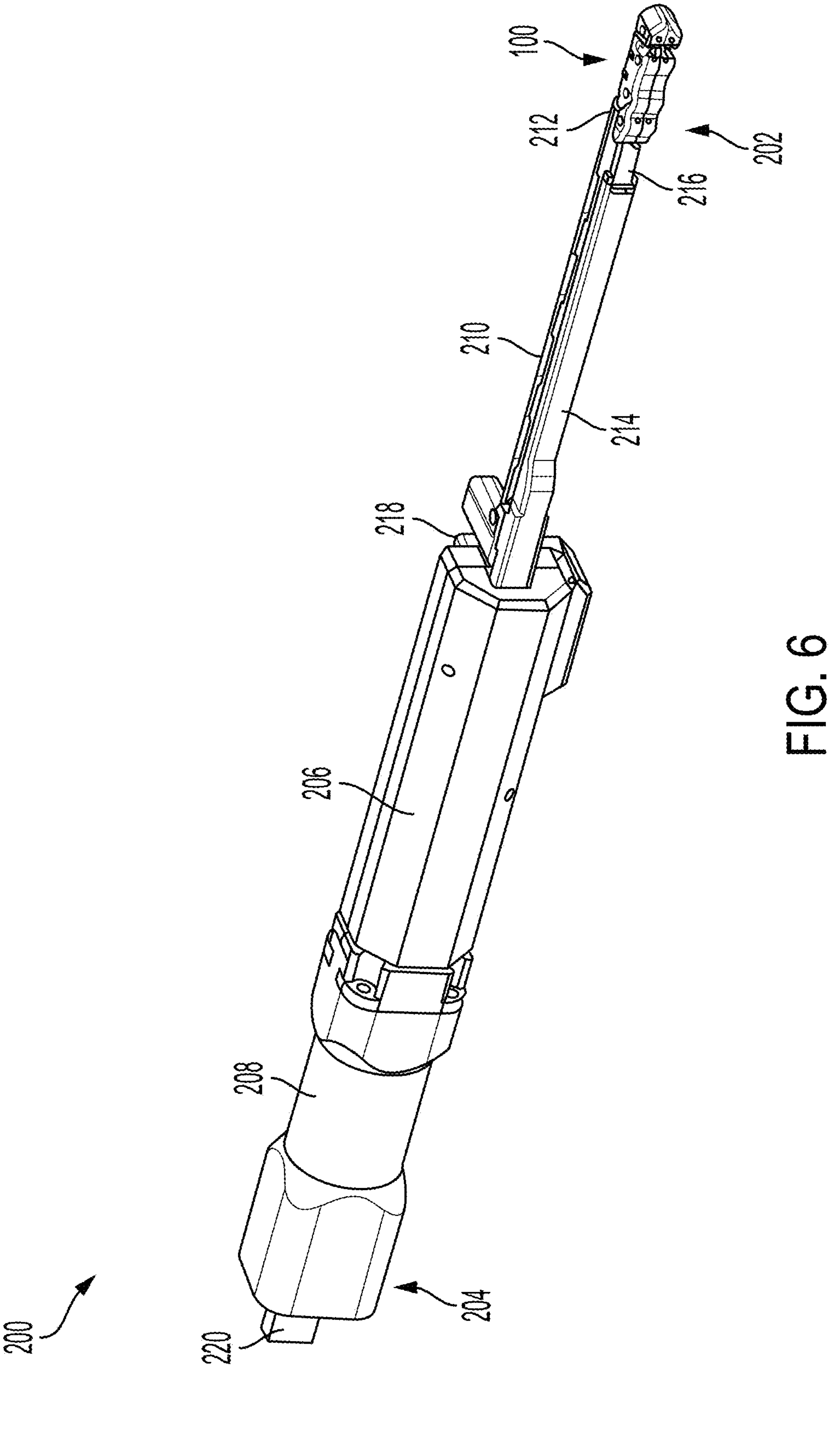
FIG. 6 depicts a perspective view of an exemplary insertion tool according to one embodiment.
Figure 7:
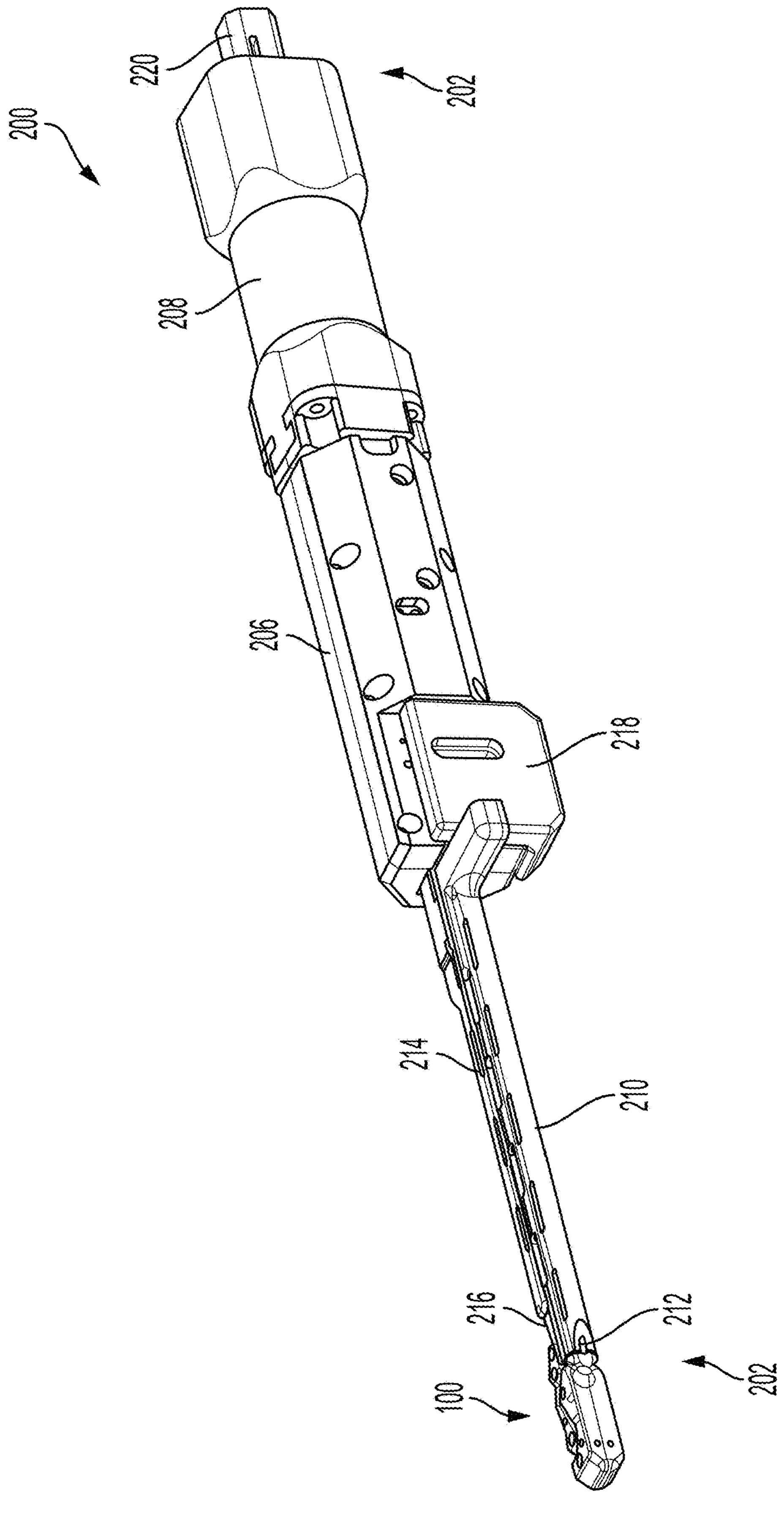
FIG. 7 depicts a perspective view of an exemplary insertion tool according to one embodiment.

Referring now to FIG. 6 and FIG. 7, an exemplary insertion tool 200 is depicted. Insertion tool 200 comprises an anterior end 202, a posterior end 204, a nonrotating handle 206, a rotating handle 208, a locking sleeve 210, tongs 212, a deployment driver 214, a driver horn 216, a backstop 218, and a driver shaft 220. Nonrotating handle 206 has a lumen through which deployment driver 214 and driver shaft 220 extends. Rotating handle 208 comprises a lumen and is rotatable about nonrotating handle 206 to advance deployment driver 214 in a posterior and anterior direction. In some embodiments, a handle (not shown) can be attached to the posterior end of rotating handle 208 to provide a larger grip for increased leverage in the rotation of rotating handle 208. In some embodiments, the posterior end of driver shaft 220 can be used as a striking surface, or be used as a connector to mount a striking cap (not shown), such that insertion tool 200 can be hammered to insert a device 100 into a vertebral space.

Figure 8:
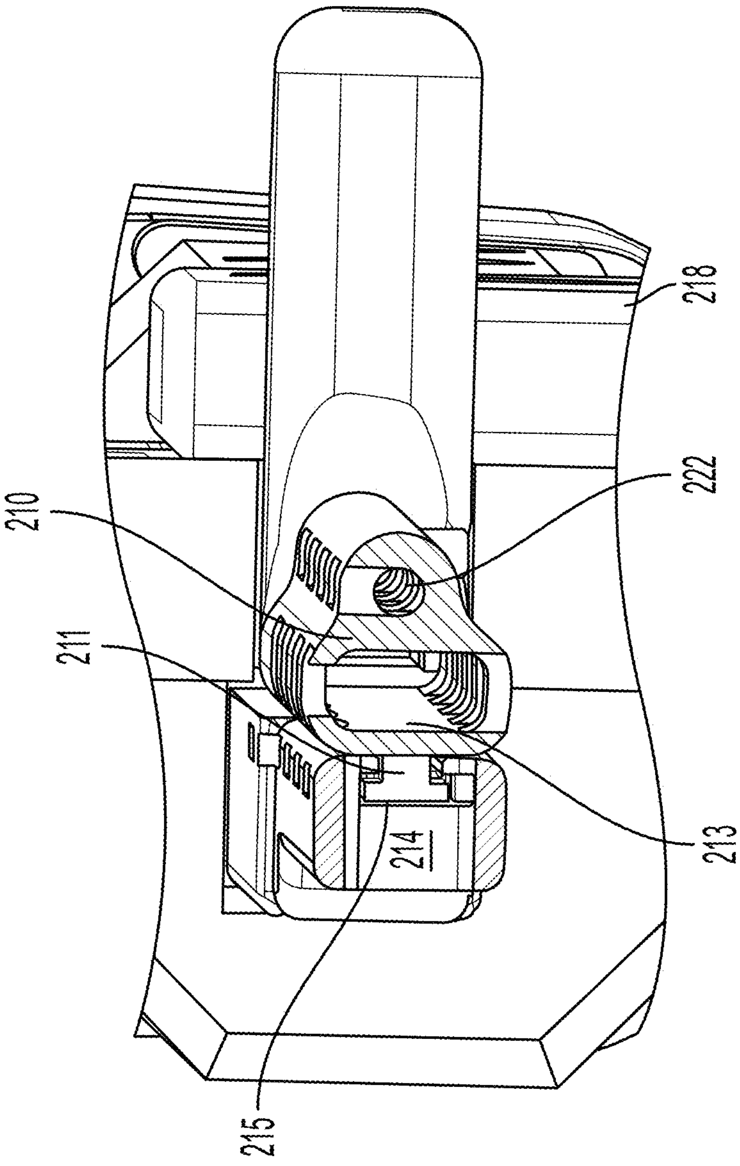
FIG. 8 depicts an anterior view of an exemplary insertion tool according to one embodiment.
Figure 9:
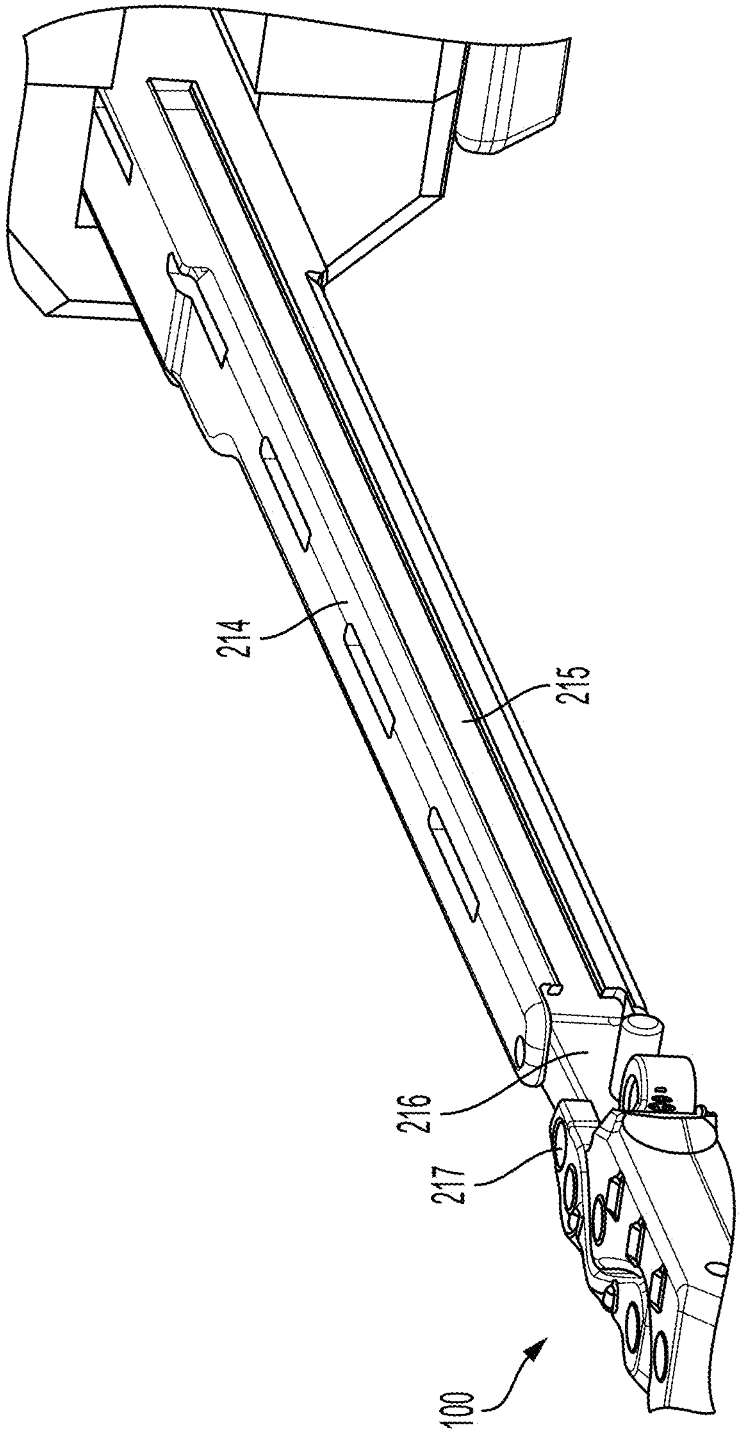
FIG. 9 depicts a perspective view of a deployment driver of an exemplary insertion tool according to one embodiment.
Figure 10:
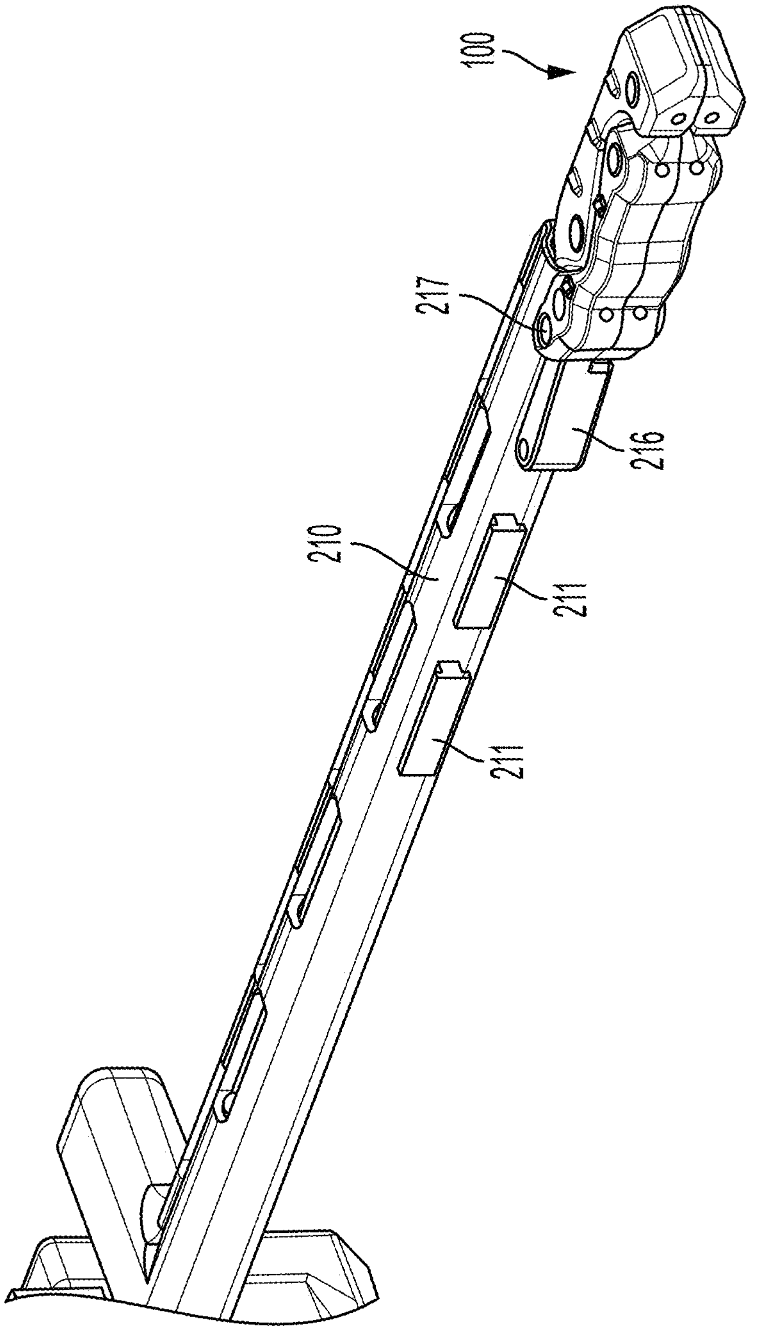
FIG. 10 depicts a perspective view of an expansion sleeve of an exemplary insertion tool according to one embodiment.
Figure 13:
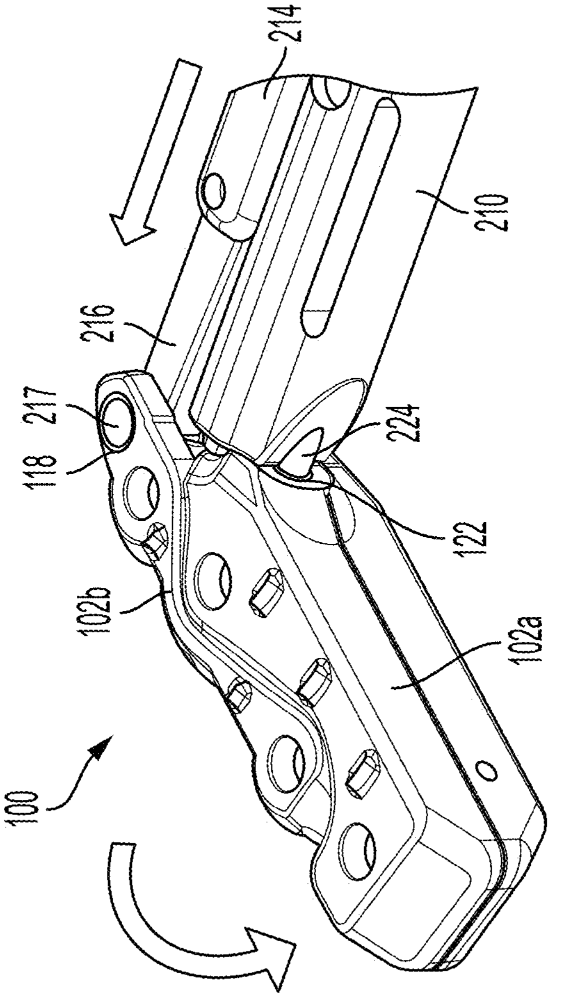
FIG. 13 depicts an articulation of an exemplary articulating expandable device using an exemplary insertion tool according to one embodiment.

Referring now to FIG. 8 through FIG. 10, locking sleeve 210 and deployment driver 214 are depicted in detail. Locking sleeve 210 comprises a tong lumen 213 sized to receive tongs 212 (as shown in FIG. 7) and a locking bit lumen 222 sized to receive a locking bit driver 224 (as shown in FIG. 13), wherein locking bit lumen 222 extends through driver shaft 220 and is accessible at a posterior end of driver shaft 220. Locking sleeve 210 comprises tabs 211 that are slidable within track 215 of deployment driver 214, such that locking sleeve 210 and deployment driver 214 are slidably engaged to each other while maintaining a flush parallel alignment between each of their longitudinal axes. Backstop 218 is provided at a posterior end of locking sleeve 210 and prevents movement in locking sleeve 210. Deployment driver 214 comprises driver horn 216 hingedly connected at its anterior end. The hinged connection permits driver horn 216 to adapt to an articulating and expanding device 100, as will be described elsewhere herein.

Figure 11:
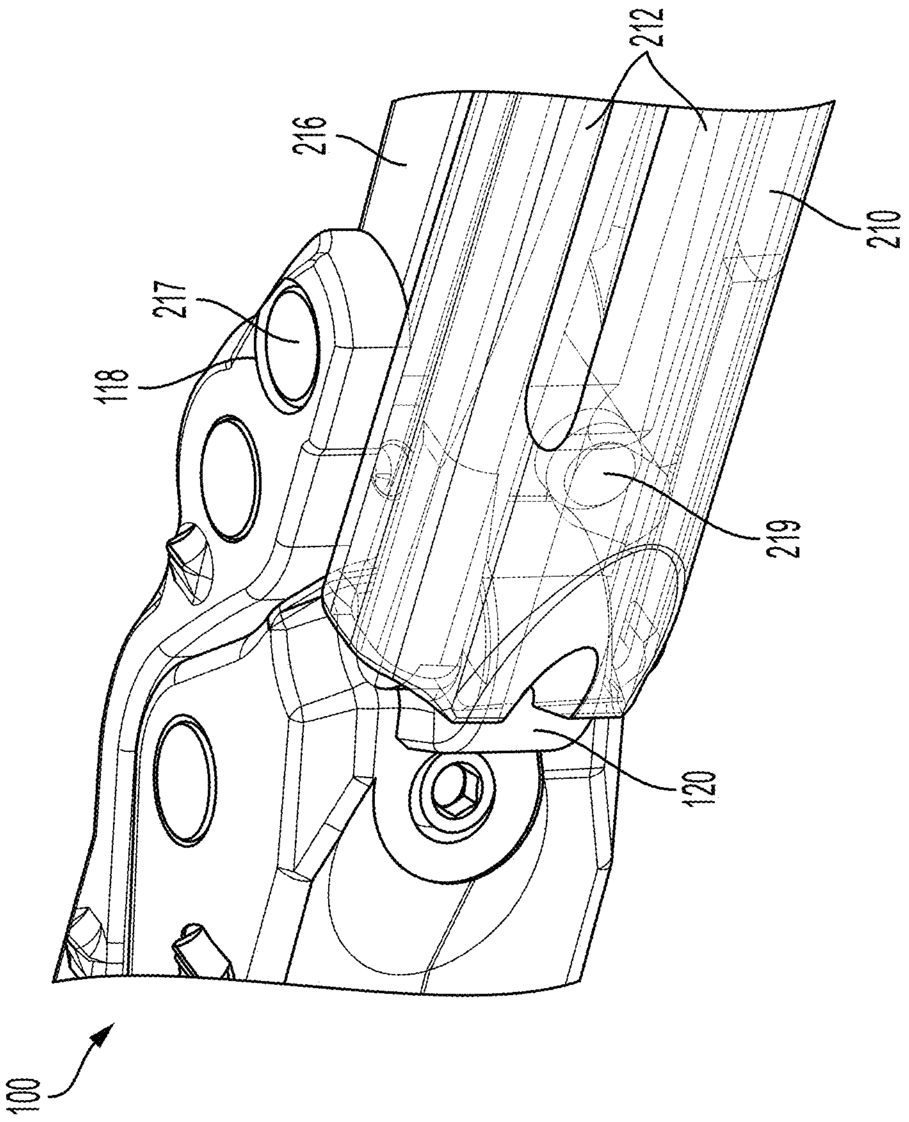
FIG. 11 depicts a partially wireframe view of an exemplary articulating expandable device loaded onto an exemplary insertion tool according to one embodiment, such that internal tongs are visible.
Figure 12:
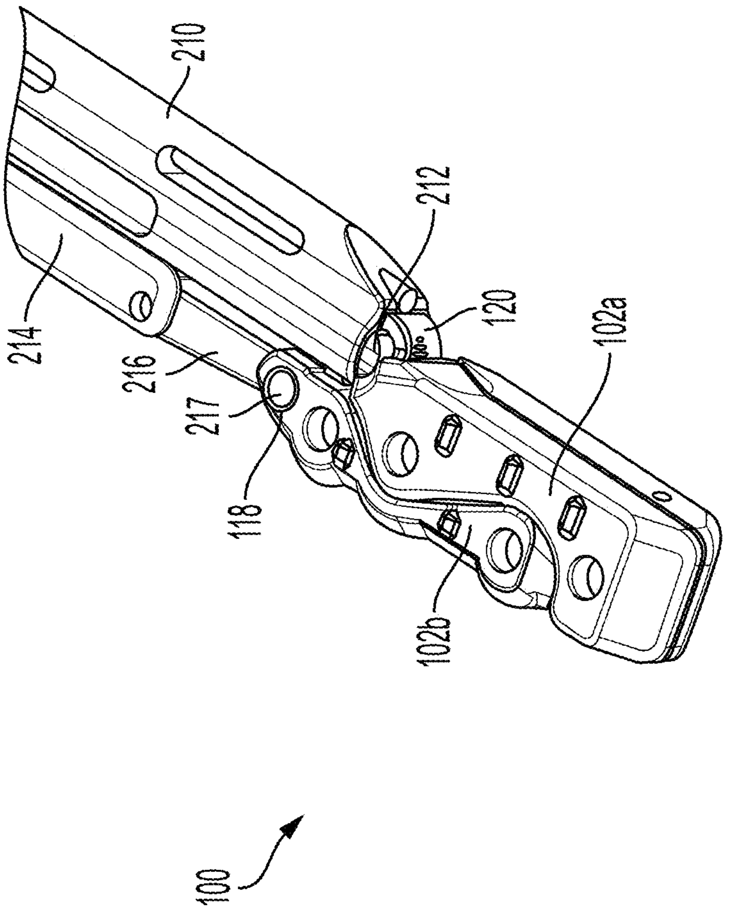
FIG. 12 depicts a magnified view of an exemplary articulating expandable device loaded onto an exemplary insertion tool according to one embodiment.

Referring now to FIG. 11, the engagement between insertion tool 200 and an articulating expandable device 100 is shown in detail. Driver horn 216 comprises peg 217 sized to fit within socket 118 of device 100. Tongs 212 immovably extend from nonrotating handle 206 in an anterior direction through tong lumen 213 of locking sleeve 210. Tongs 212 are expandable at anterior end 202, enabling the anterior end of tongs 212 to hingedly engage connector 120 of expandable device 100. Locking sleeve 210 comprises a wedge 219 positioned between each member of tongs 212, such that sliding locking sleeve 210 in a posterior direction forces tongs 212 open.

Referring now to FIG. 12 through FIG. 15, the articulation and expansion of an articulating expandable device 100 using an insertion tool 200 is now described. As described above and depicted in FIG. 12, a device 100 can be engaged to anterior end 202 of an insertion tool 200 by clamping the anterior end of tongs 212 around connector 120. Tongs 212 are hingedly engaged to connector 120 by advancing locking sleeve 210 into an anterior-most position, and locking sleeve 210 is locked in place by engaging backstop 218. Deployment driver 214 can be engaged to device 100 by inserting peg 217 of driver horn 216 into socket 118.

In FIG. 13, rotating handle 208 is rotated about nonrotating handle 206 to advance deployment driver 214 in an anterior direction, whereupon device 100 articulates about the hinged engagement between an arm and tongs 212 (here, arm 102*a*). The full articulation of device 100 brings locking bit 122 to bear with locking bit lumen 222, such that locking bit 122 is accessible by a locking bit driver 224 extending through driver shaft 220 and locking sleeve 210 by way of locking bit lumen 222. In some embodiments, the articulation of device 100 relative to device 200 is predetermined, wherein an angle of articulation is defined by a surface facet of device 100 around locking bit 122 and a surface facet of locking sleeve 210. In some embodiments, the articulation of device 100 relative to device 200 is variable. For example, locking sleeve 210 can comprise a sliding surface facet that can meet a surface facet of locking sleeve 210 in any position, or locking bit driver 224 can be positioned at a fixed location and act as a physical stop for an articulating device 100. In various embodiments, the articulation of device 100 relative to device 200 can be described in terms of an angle between a longitudinal axis of device 100 and a longitudinal axis of device 200. The angle can be any angle between about 1 and 360 degrees. In some embodiments, the angle is between about 1 and 180 degrees. In some embodiments, the angle is between about 181 and 360 degrees. In certain embodiments, device 100 and device 200 can be provided in a mirrored configuration to achieve articulation in an opposing angle between about 1 and 360 degrees, between about 1 and 180 degrees, or between about 181 and 360 degrees.

Figure 14:
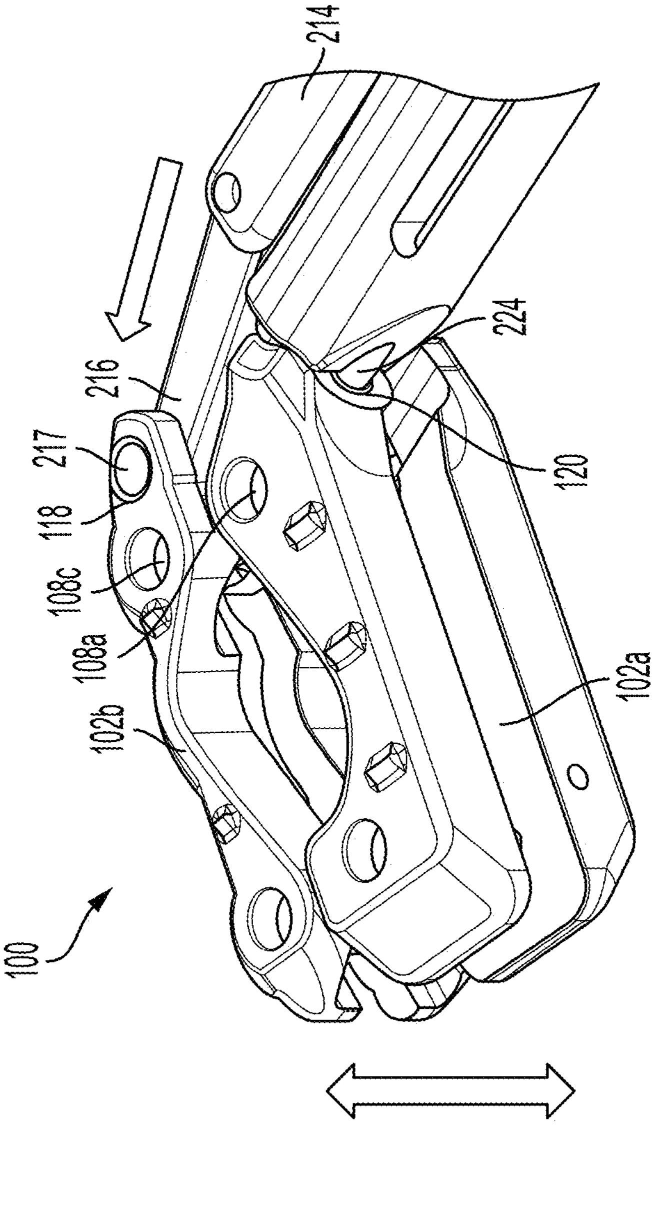
FIG. 14 depicts a deployment of an exemplary articulating expandable device using an exemplary insertion tool according to one embodiment.

In FIG. 14, device 100 is expanded by further advancing deployment driver 214 in an anterior direction by rotating handle 208 being rotated about nonrotating handle 206. Further anterior advancement of deployment driver 214 pushes driver horn 216 and arm 102*b* in an anterior direction while anterior movement in arm 102*a* is prevented by tongs 212. The relocation of arm 102*b* relative to arm 102*a* leads to a synchronized series of movements where pins 112 in arm 102*b* moving through the pin guides of bolt 108*c* rotates the associated bolts 108 as well as the opposing bolts 108 connected by connecting rods 110, positioning all pins 112 in their open positions. Device 100 can be closed by twisting rotating handle 208 in an opposite direction, which retracts deployment driver 214 and arm 102*b* in a posterior direction and causes the aforementioned movements to be carried out in reverse. Device 100 can be locked into any position between its open configuration and its closed configuration by driving locking bit 122 with locking bit driver 224, whereupon locking bit 122 drives into bolt 108*a*, locking its rotation and consequently the movement of every other interconnected piece.

Figure 15:
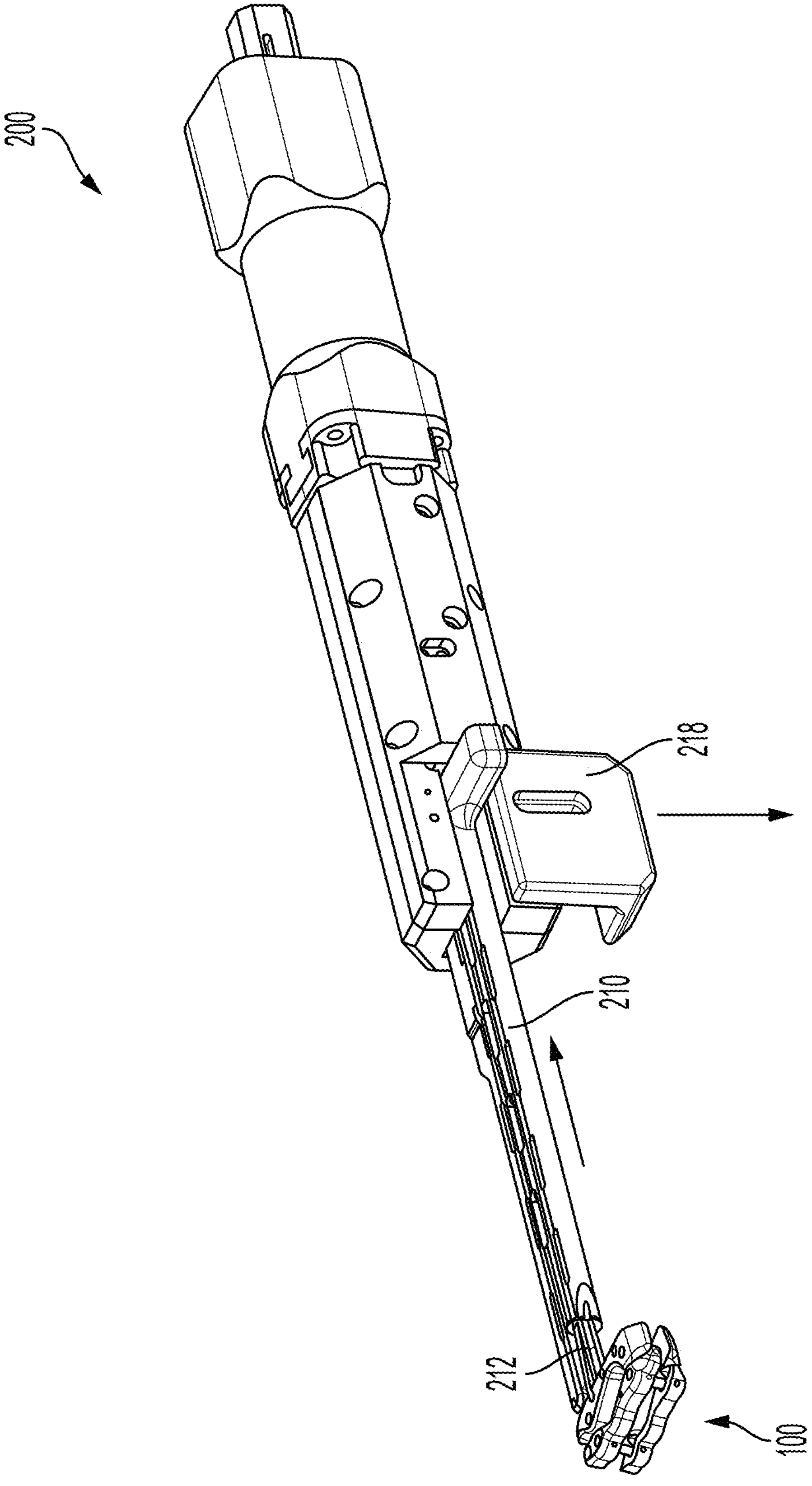
FIG. 15 depicts an actuation of an exemplary insertion tool for releasing an exemplary articulating expandable device according to one embodiment.

In FIG. 15, backstop 218 is disengaged, allowing locking sleeve 210 to be slid back in a posterior direction. Sliding locking sleeve 210 also slides wedge 219 against tongs 212, separating each member of tongs 212 and releasing tongs 212 from connector 120 and from device 100.

Methods of Making

The devices of the present invention can be made using any suitable method known in the art. The method of making may vary depending on the materials used. For example, devices substantially comprising a metal may be milled from a larger block of metal or may be cast from molten metal. Likewise, components substantially comprising a plastic or polymer may be milled from a larger block, cast, or injection molded. In some embodiments, the devices may be made using 3D printing or other additive manufacturing techniques commonly used in the art.

Methods of Use

The present invention also includes methods of using articulating expandable devices. As described elsewhere herein, the articulating expandable devices of the present invention can navigate corners and are switchable between a compact closed configuration and an expanded open configuration and are capable of withstanding compressive forces in the expanded open configuration. The expandable devices are useful in any application requiring the maintenance of a space under load.

In one embodiment, the articulating expandable devices of the present invention are useful as interbody devices. For example, in the case of intervertebral disc removal in a patient, the articulating expandable devices of the present invention are useful as an interbody device to complete a spinal fusion procedure. Contemplated procedures include but are not limited to posterior lumbar interbody fusion (PLIF) and transforaminal lumbar interbody fusion (TLIF), lateral (trans-psoas) approaches, oblique approaches, and anterior lumbar interbody fusion (ALIF) procedures. The rigidity of the articulating expandable devices enables stable, long term maintenance of a disc space void in an open configuration. The articulating expandable devices can also be inserted in a less invasive manner due to their compact closed configuration. In a typical spinal fusion procedure, a skin incision is made adjacent to an intervertebral disc that requires removal. The disc space is identified, and the annulus of the disc is opened. Any suitable tools and techniques may be used to evacuate the intervertebral disc from the disc space and to prepare the adjoining bony endplates for good bony ingrowth.

Figure 16:
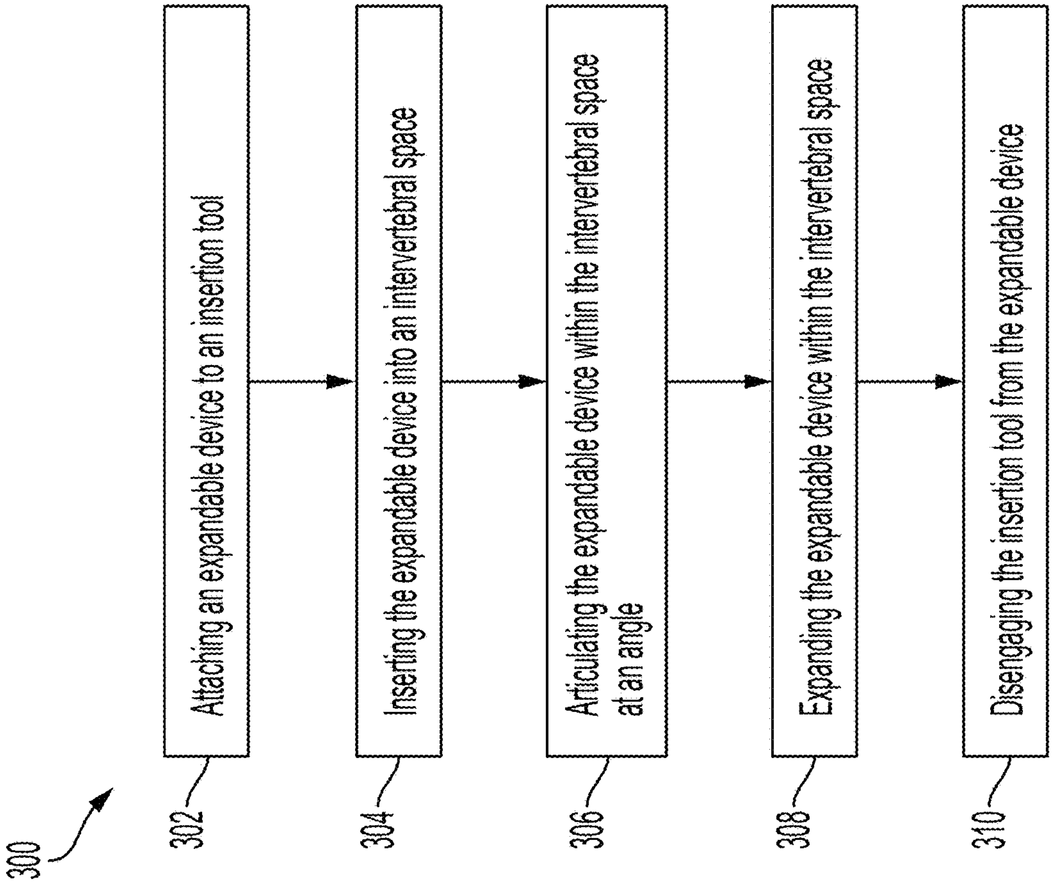
FIG. 16 is a flowchart of an exemplary method of using an articulating expandable body device in a spinal fusion procedure according to one embodiment.

Once the disc space has been prepared, an expandable device of the present invention may be used to fuse the spine. Referring now to FIG. 16, an exemplary method 300 of inserting an articulating expandable device into a disc space is depicted. In step 302, an expandable device in a closed configuration is attached to an insertion tool. In step 304, the expandable device is inserted into an intervertebral space. In step 306, the expandable device is articulated within the intervertebral space at an angle. The angle can be any angle between about 1 and 360 degrees, 1 and 180 degrees, or 181 and 360 degrees. In step 308, the expandable device is expanded with the insertion tool within the intervertebral space. In step 310, the insertion tool is disengaged from the expandable device. In various embodiments, the expandable device can be packed with one or more components at any step to encourage healing, including bone tissue, stem cells, anti-inflammatoires, antibiotics, antivirals, and the like. Any suitable imaging technique, such as ultrasound or x-ray, may be used during any step to confirm proper placement of the expandable device within the intervertebral space.

In other embodiments, the expandable devices of the present invention are useful as mechanical spacers. For example, in any various mechanical applications, there may be a need to temporarily or permanently provide a support within a space. As described elsewhere herein, the expandable devices of the present invention can further include one or more sensors for monitoring performance, including temperature sensors, gyroscopes, pressure sensors, corrosion sensors, and the like.

Figure 17B:
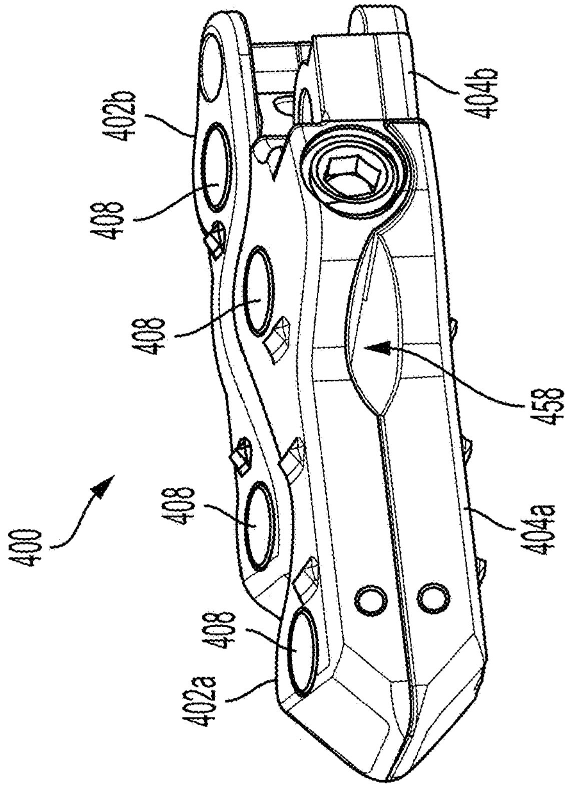
FIG. 17A and FIG. 17B are perspective views of an articulating expandable device according to one embodiment.
Figure 17A:
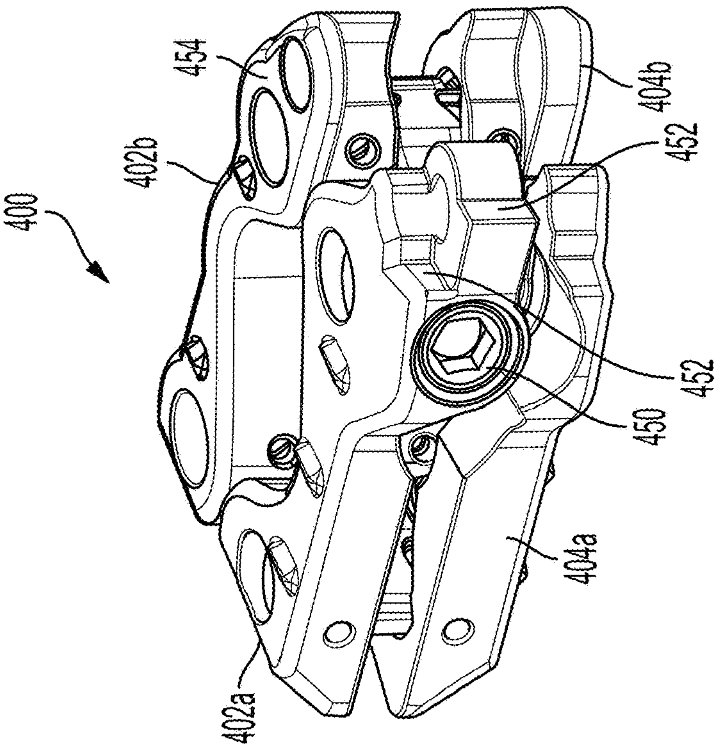

With reference now to FIGS. 17A and 17B, an exemplary articulating expandable device 300 is depicted according to one embodiment. Similar to the structure and functionality of the embodiment of device 100 described above, device 400 comprises four arms (superior first arm 402*a*, superior second arm 402*b*, inferior third arm 404*a*, and inferior fourth arm 404*b*) and four movable bolts 408. Device 400 relies on the arrangement of bolts 408, as well as pins, pin guides, cams, and opposing cam faces to synchronize the simultaneous movement between each arm 402*a*, 402*b*, 404*a*, and 404*b* using the same mechanical principals described with respect to the embodiment of device 100. Shifting expandable device 400 from a closed configuration to an open configuration separates superior arms 402*a* and 402*b* from inferior arms 404*a* and 404*b* at the same rate and distance. Shifting expandable device 400 from a closed configuration to an open configuration also laterally separates arms 402*a* and 404*a* from arms 402*b* and 404*b*. In one embodiment, the locking set screw 452 can be enlarged in one embodiment, having enlarged diameter and drive socket sizing, which for example can provide enhanced tool interface, torquing and locking. In one embodiment, deployment stops 454 are formed on outer surfaces of the arms to engage with the side of the inserter. This interface geometry provides a more positive, pronounced and reliable stopping mechanism to allow the device to be fully deployed without tool slippage. The arms can also be formed to include a lordosis adjustable plate and arm geometry 456. In one embodiment, the arms were made so that 0-15 degrees of lordosis can be added. Other suitable ranges can be implemented. The range can be chosen before manufacturing and customized based on patent anatomy and the surgical approach and strategy. In one embodiment, a bone graft window 458 is configured into one or more of the arms. The bone graft window 458 can for example be formed from a first recess in the superior first arm 402*a* and a second recess formed in the inferior third arm 404*a*. This allows the inserting tool to drive bone graft to the internal area of the implant regardless of deployment amplitude.

Figure 18A:
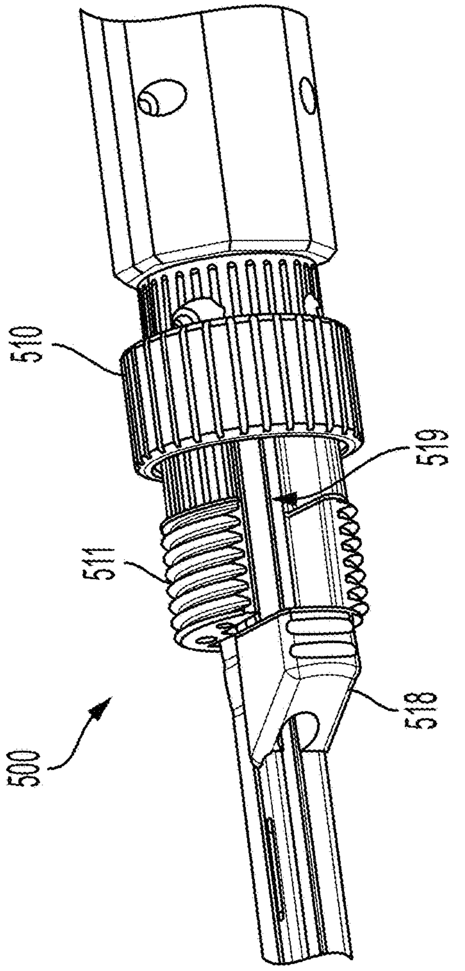
FIG. 18A and FIG. 18B are perspective views of a threaded locking sleeve according to one embodiment.
Figure 18B:
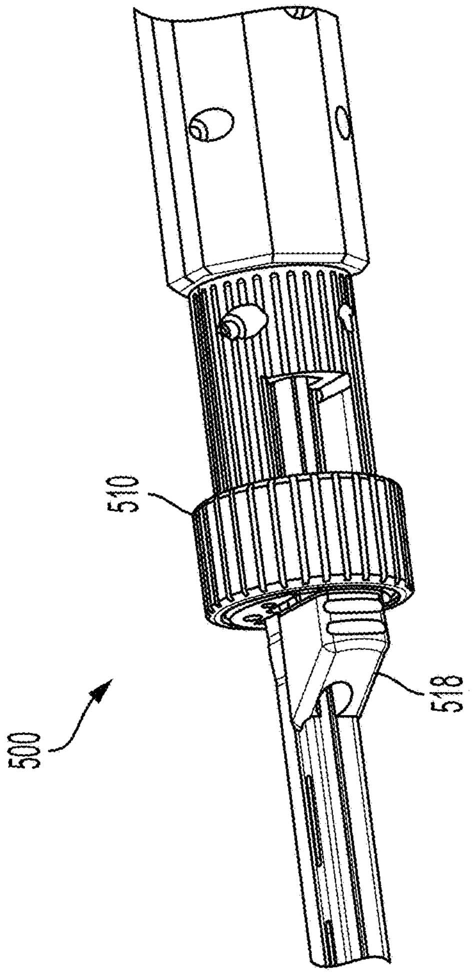
Figure 19:
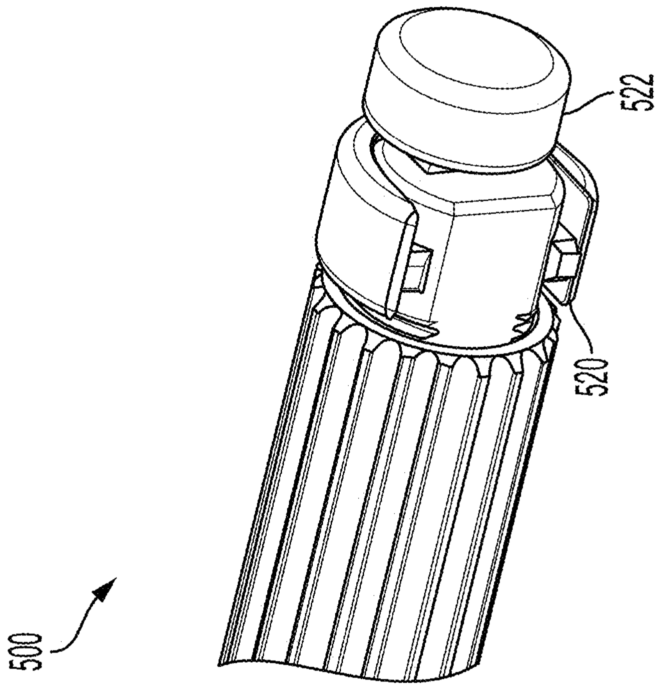
FIG. 19 is a perspective view of a locking clip and removable hammering protector according to one embodiment.
Figure 20:
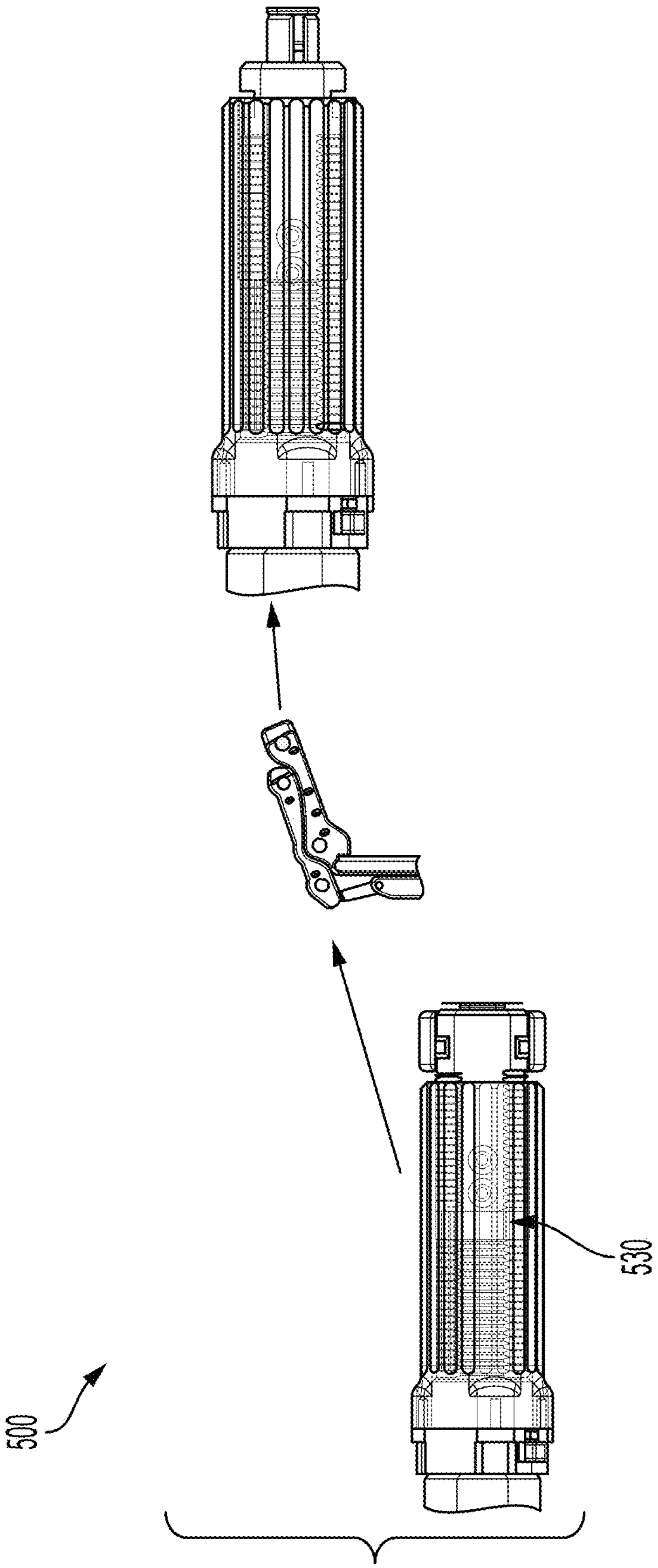
FIG. 20 is a side view of a non-continuous thread and gap configuration that allows passive or hammered turning of the implant to a predetermined degree point, after which, the threads begin to engage so the implant can be deployed.

Referring now to FIGS. 18A-20, embodiments of an exemplary insertion tool 500 are depicted. The insertion tool 500 is designed to operate substantially similar to the embodiment of the insertion tool 200 described above with certain modifications. With reference now to FIGS. 18A and 18B, a threaded locking sleeve 510 is utilized to hold the tong sleeve and tongs more positively and reliably on implant, resulting in a better hold on the implant. The locking sleeve 510 can interface with threads 511 along a fully threaded portion. A backstop 518 interfaces with the locking sleeve 510 to prevent movement of the locking sleeve 510. As shown in FIG. 19, a locking clip 520 can be utilized to keep the implant from turning or deploying during initial insertion. The locking clip 520 locks the implant parallel to the inserter so that it can be hammered into place. The removable hammering protector 522 can be placed on the end to protect the device and direct hammer blows to the correct position. With reference now to FIG. 20, in one embodiment, non-continuous threads and a thread gap 530 are added to allow for passive or hammered turning of the implant to the 70 degree point shown. After which, the threads begin to engage so the implant can be deployed. Accordingly, a thread gap can be disposed to correspond to a predetermined implant angle, with threads continuing at the point of implant deployment.

Figure 21:
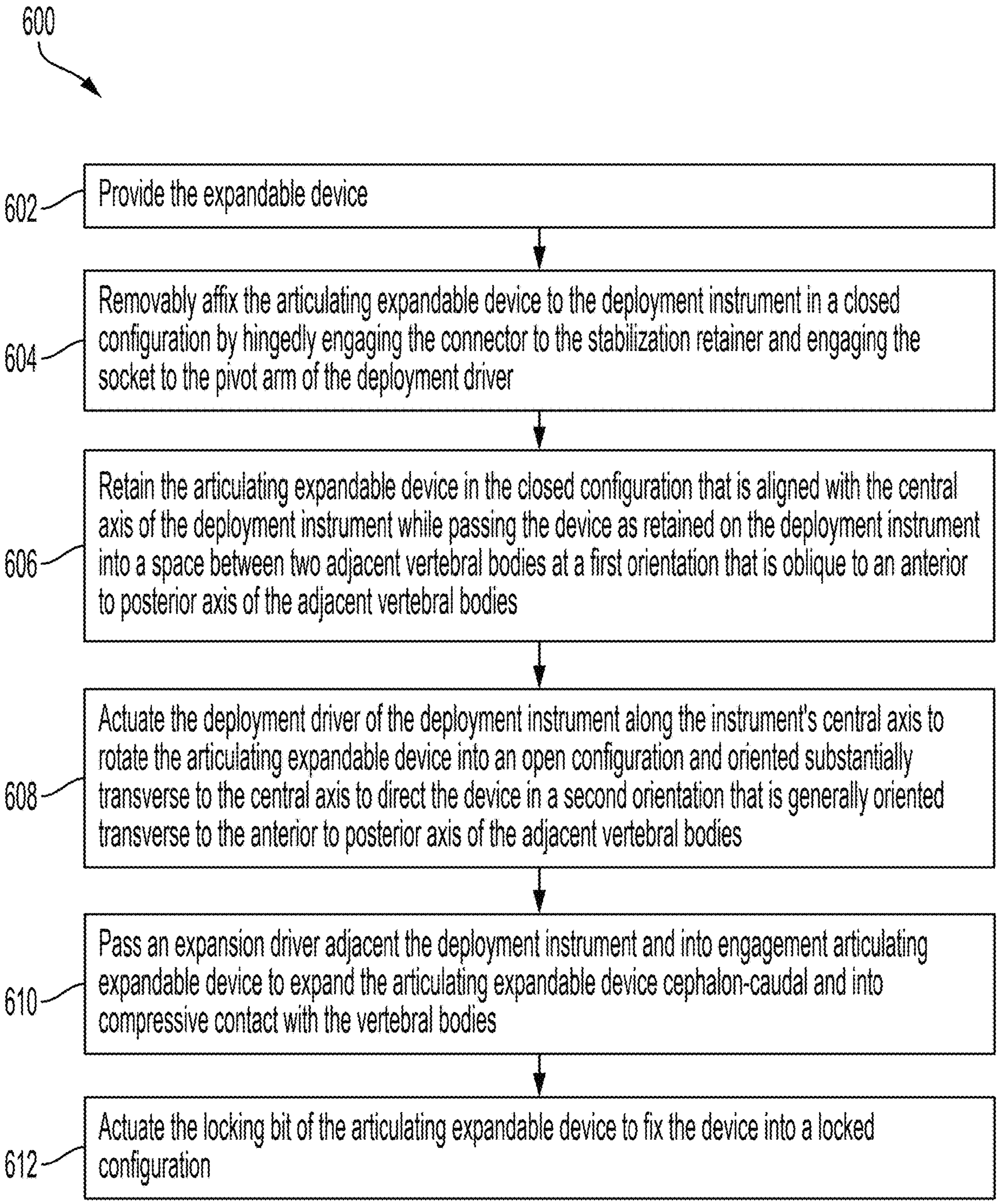
FIG. 21 is a flow chart of a method for deployment of an articulating and expandable device into a space between adjacent vertebral bodies according to one embodiment.

With reference now to FIG. 21, a method 600 for deployment of an articulating and expandable device into a space between adjacent vertebral bodies is described according to one embodiment. The method includes the steps of providing the expandable device having a first and a second superior arm and a first and a second inferior arm, the first superior arm further comprising a hinged connector extending from its posterior end, and the second superior arm further comprising a socket extending from its posterior end 602, removably affixing the articulating expandable device to the deployment instrument in a closed configuration by hingedly engaging the connector to the stabilization retainer and engaging the socket to the pivot arm of the deployment driver 604, retaining the articulating expandable device in the closed configuration that is aligned with the central axis of the deployment instrument while passing the device as retained on the deployment instrument into a space between two adjacent vertebral bodies at a first orientation that is oblique to an anterior to posterior axis of the adjacent vertebral bodies 606, actuating the deployment driver of the deployment instrument along the instrument's central axis to rotate the articulating expandable device into an open configuration and oriented substantially transverse to the central axis to direct the device in a second orientation that is generally oriented transverse to the anterior to posterior axis of the adjacent vertebral bodies 608, passing an expansion driver adjacent the deployment instrument and into engagement articulating expandable device to expand the articulating expandable device cephalon-caudal and into compressive contact with the vertebral bodies 610, and actuating the locking bit of the articulating expandable device to fix the device into a locked configuration 612. In one embodiment, the method includes initially driving the articulating expandable device into the surgical site by hammering on a slap hammer surface at the proximal handle of the deployment instrument. In one embodiment, the method includes actuating release of the stabilization retainer from the articulating expandable device. In one embodiment, the method includes expanding the articulating expandable device results in the release of the pivot arm of the deployment driver.

Additionally, in one embodiment, a deployment instrument includes a proximal handle, a stabilization retainer extending parallel to a central axis from the proximal handle to a distal end of the deployment instrument, and a deployment driver extending parallel to the stabilization retainer along the central axis, the deployment driver including at its distal end a hingedly connected pivot arm, wherein at least one of the stabilization retainer and deployment driver is translatable along the central axis. In one embodiment, only the deployment driver is translatable along the central axis. In one embodiment, the deployment driver is slidably translatable along the central axis. In one embodiment, the proximal handle includes one or more features selected from the group consisting of (i) an actuator that drives translation of the deployment driver along the central axis, the actuator comprising a mechanism selected from the group consisting of sliding rail, ratchet, worm gear, screw, cam and follower, lever, gear, spring, and combinations thereof; (ii) a slap hammer surface; and (iii) combinations thereof. In one embodiment, the proximal handle includes an actuator that drives translation of the deployment driver along the central axis, the actuator comprising corresponding threaded engagement between a proximal portion of the deployment driver and a housing portion of the proximal handle, wherein the threaded engagement can drive movement of the deployment driver along the central axis. In one embodiment, the proximal handle includes a lock that prevents actuation of translation of the deployment driver along the central axis. In one embodiment, one or both of the stabilization retainer and the pivot arm of the deployment is forked at its distal end the forks including opposing pins that form a hinged connector with a pivot axis. In one embodiment, only the stabilization retainer is forked at its distal end, the fork including opposing pins that form a hinged connector with a pivot axis. In one embodiment, the stabilization retainer includes at its distal end a pair of retaining pins oriented along an axis that is transverse to the central axis and forming a hinged connector. In one embodiment, the stabilization retainer includes at its distal end a pair of opposing fork arms and a pair of opposing retaining pins, each one of the pair of retaining pins oriented distally on a fork arm, the opposing pair of retaining pins forming a hinged connector. In one embodiment, the device includes a locking sleeve that is slidable along the central axis over the stabilization retainer to releasably compress the opposing fork arms. In one embodiment, the locking sleeve comprises a wedge that is positionable between the opposing fork arms, such that when the wedge is positioned most distally relative to the fork arms, the fork arms are in a relaxed orientation, and when the wedge is moved proximally by translation of the sleeve proximally along the stabilization retainer, the wedge contacts the opposing fork arms into an expanded orientation and the opposing retaining pins are displaced away from each other. In one embodiment, the proximal handle includes a lock that retains the locking sleeve in place to compress the opposing fork arms. In one embodiment, the hingedly connected pivot arm on the deployment driver includes a pair of retaining pins oriented along an axis that is transverse to the central axis and forming a hinged connector, wherein each of the retaining pins projects outward from the pivot arm. In one embodiment, the hingedly connected pivot arm on the deployment driver includes at its distal end a pair of opposing fork arms and a pair of opposing retaining pins, each one of the pair of retaining pins oriented distally on a fork arm, the pair of opposing retaining pins forming a hinged connector.

In one embodiment, a deployment instrument, includes a proximal handle, a stabilization retainer extending parallel to a central axis from the proximal handle to a distal end of the deployment instrument, the stabilization retainer including at its distal end a first pair of retaining pins oriented along an axis that is transverse to the central axis, and a deployment driver extending parallel to the stabilization retainer along the central axis, the deployment driver including at its distal end a hingedly connected pivot arm, the pivot arm including at a distal end a second pair of retaining pins, wherein at least one of the stabilization retainer and deployment driver is slidably translatable along the central axis.

In one embodiment, a deployment instrument includes a proximal handle, a stabilization retainer extending parallel to a central axis from the proximal handle to a distal end of the deployment instrument, the stabilization retainer including at its distal end a pair of opposing fork arms and a pair of opposing retaining pins, each one of the pair of retaining pins oriented distally on a fork arm, the opposing pair of retaining pins forming a hinged connector, a locking sleeve that is slidable along the central axis over the stabilization retainer to releasably compress the opposing fork arms, the locking sleeve comprising a wedge that is positionable between the opposing fork arms, such that when the wedge is positioned most distally relative to the fork arms, the fork arms are in a relaxed orientation, and when the wedge is moved proximally by translation of the sleeve proximally along the stabilization retainer, the wedge contacts the opposing fork arms into an expanded orientation and the opposing retaining pins are displaced away from each other, and a deployment driver extending parallel to the stabilization retainer along the central axis, the deployment driver including at its distal end a hingedly connected pivot arm, the pivot arm including at its distal end a pair of retaining pins oriented along an axis that is transverse to the central axis and forming a hinged connector, wherein each of the retaining pins projects outward from the pivot arm, wherein the handle includes an actuator that drives translation of the deployment driver along the central axis, the actuator comprising a mechanism the proximal handle includes one or more features selected from the group consisting of (i) an actuator that drives translation of the deployment driver along the central axis, the actuator comprising a mechanism selected from the group consisting of sliding rail, ratchet, worm gear, screw, cam and follower, lever, gear, spring, and combinations thereof; (ii) a slap hammer surface; and (iii) combinations thereof.

Embodiments of the invention may also be embodied as a device kit, or included as a component of a device kit. For example, in one embodiment, an articulating expandable device kit includes an articulating expandable device having a first and a second superior arm and a first and a second inferior arm, the first superior arm further comprising a hinged connector extending from its posterior end, and the second superior arm further comprising a socket extending from its posterior end; and a deployment instrument having a proximal handle, a stabilization retainer extending parallel to a central axis from the proximal handle to a distal end of the deployment instrument, and a deployment driver extending parallel to the stabilization retainer along the central axis, the deployment driver including at its distal end a hingedly connected pivot arm, wherein at least one of the stabilization retainer and deployment driver is translatable along the central axis. In one embodiment, the articulating expandable device is configured to removably attach to the deployment instrument in a closed configuration by hingedly engaging the connector to the stabilization retainer and engaging the socket to the pivot arm of the deployment driver wherein the articulating expandable device includes positive stop features that retain the articulating expandable device in the closed configuration that is aligned with the central axis of the deployment instrument, and wherein actuating translation of the deployment driver along the central axis to drive the pivot arm distally, the pivot arm is driven to rotate driving the engaged socket to translate the articulating expandable device into an open configuration and oriented substantially transverse to the central axis.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An articulating expandable device, comprising:

a first and a second superior arm and a first and a second inferior arm;

the first superior arm further comprising a hinged connection extending from its posterior end and configured to simultaneously pivot the first and second superior arm and the first and second inferior arm, wherein a portion of the hinged connection moves independently along a different axis during the simultaneous pivot; and the second superior arm further comprising a driver connection extending from its posterior end and is configured to actuate the simultaneous pivot, wherein a portion of the driver connection moves independently along a different axis during the simultaneous pivot;

wherein the first and second superior arm and the first and second inferior arm are configured to expand away from a first plane, and wherein the hinged connection and the first and second superior arm are configured to pivot along a second plane.

2. The device of claim 1, wherein each arm possesses an anterior and a posterior end and a top and a bottom surface, and each arm having an anterior and posterior opening through the top and bottom surface, wherein the first superior arm is positioned over the first inferior arm with anterior and posterior openings in alignment, and the second superior arm is positioned over the second inferior arm with anterior and posterior openings in alignment.

3. The device of claim 2, further comprising:

four cylindrical bolts positioned within each of the openings of the arms;

a first rod connecting each of the bolts positioned within the anterior openings of the arms; and a second rod connecting each of the bolts positioned within the posterior openings of the arms.

4. The device of claim 3, the cylindrical bolts further comprising:

a top end, a bottom end, an outer surface, and at least one upper curved slot and at least one lower curved slot extending through each bolt, wherein each curved slot has a closed position near a center of each bolt, each of the at least one upper curved slot has an open position near the top end of each bolt, and each of the at least one lower curved slot has an open position near the bottom end of each bolt.

5. The device of claim 4, further comprising:

a plurality of pins, each pin connected to an inner surface of each of the openings of the arms and slidably engaged to a curved slot of the bolt positioned within the respective opening.

6. The device of claim 5, wherein each of the four arms are substantially parallel to each other in a closed configuration.

7. The device of claim 6, wherein the four arms are movable about the four bolts while maintaining substantially parallel alignment to each other.

8. The device of claim 5, wherein the device comprises a closed configuration that positions the four arms adjacent to each other and positions the plurality of pins near the center of each bolt.

9. The device of claim 5, wherein the device comprises an open configuration that positions the four arms away from each other and positions the plurality of pins near the top and bottom ends of each bolt.

10. The device of claim 5, wherein at least one arm comprises a locking bit drivable into a bolt.

11. The device of claim 3, wherein at least one arm comprises a locking bit drivable into a bolt.

12. An articulating expandable device kit comprising:

the device of claim 1; and an insertion tool, comprising:

a posterior handle having a rotating section, a nonrotating section, and a lumen running throughout;

an expandable pair of tongs extending from the nonrotating section in an anterior direction, the tongs having a hinged anterior connector;

a locking sleeve slidable over the pair of tongs; and an elongate deployment driver positioned within the lumen of the housing, the deployment driver having a hingedly connected driver horn.

13. The kit of claim 12, wherein anterior and posterior movement of the locking sleeve is lockable using a backstop.

14. The kit of claim 12, wherein actuating the rotating section of the housing moves the deployment driver in an anterior or posterior direction.

15. The kit of claim 12, wherein the locking sleeve comprises a wedge positioned between each member of the pair of tongs, such that posterior sliding of the locking sleeve expands the pair of tongs.

* * * * *